United States Patent
Brauker et al.

(10) Patent No.: US 6,517,571 B1
(45) Date of Patent: *Feb. 11, 2003

(54) VASCULAR GRAFT WITH IMPROVED FLOW SURFACES

(75) Inventors: James Howard Brauker, Flagstaff, AZ (US); Leslie Charles Butters, Flagstaff, AZ (US); Daniel Francis Davidson, Flagstaff, AZ (US); Mark Joseph Ulm, Flagstaff, AZ (US)

(73) Assignee: Gore Enterprise Holdings, Inc., Newark, DE (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/235,214

(22) Filed: Jan. 22, 1999

(51) Int. Cl.[7] ................................................. A61F 2/06
(52) U.S. Cl. ........................................................ 623/1.13
(58) Field of Search .............................. 623/1, 11, 12; 606/108, 191, 194, 195, 198

(56) References Cited

U.S. PATENT DOCUMENTS

| | | |
|---|---|---|
| 3,914,802 A | 10/1975 | Reick |
| 3,953,566 A | 4/1976 | Gore |
| 4,082,893 A | 4/1978 | Okita |

(List continued on next page.)

FOREIGN PATENT DOCUMENTS

| | | |
|---|---|---|
| EP | 266035 | 4/1988 |
| EP | 790042 | 8/1997 |
| JP | 5474514 | 6/1979 |
| JP | 5925725 | 2/1984 |
| WO | 9505555 | 2/1995 |
| WO | 9639994 | 12/1996 |
| WO | 9826731 | 6/1998 |

OTHER PUBLICATIONS

Sawyer PN et al. Vascular Prostheses: Innovative Properties. ASTM Symposium Nov. 27–28 1984.

Impants and Devices in *Biomaterials Science An Introduction To Materials In Medicine*, ed. Ratner BD et al. San Diego: Academic Press 1996; 448–450.

Boretos JW. Cellular Polymers for Medical Use: The Vital Role of Porosity and Permeability. Cellular Polymers 1984; 3:345–358.

Branson DF et al. Expanded Polytetrafluoroethylene as a Microvascular Graft: A Study of Four Fibril Lengths. Plastic Reconstructive Surgery 1985; 76(5) 754–763.

Doi K., Matsuda T. Significance of porosity and compliance of microporous, polyurethane-based microarterial vessel on neoarterial wall regeneration. Journal of Biomed Mater Res 1997; 37:573–584.

(List continued on next page.)

Primary Examiner—Michael J. Milano
Assistant Examiner—Vy Q. Bui
(74) Attorney, Agent, or Firm—Wayne House

(57) ABSTRACT

An ePTFE vascular graft having a smooth PTFE luminal surface which is substantially non-adhesive to occlusive blood components. Preferably the graft is a longitudinally extruded and expanded ePTFE tube of about 10–30 microns mean fibril length and is provided with a luminal surface covering of an ePTFE film of small mean fibril length (5 microns of less) which provides the smooth luminal PTFE surface. The graft is anticipated to be particularly effective as a small diameter graft (6 mm or smaller). It is anticipated to have utility as a conventional vascular graft, as a cardiovascular patch and as an intraluminal vascular graft and as a covering for stents.

86 Claims, 10 Drawing Sheets

U.S. PATENT DOCUMENTS

| | | | |
|---|---|---|---|
| 4,177,334 A | | 12/1979 | Okita |
| 4,187,390 A | | 2/1980 | Gore |
| 4,194,041 A | | 3/1980 | Gore et al. |
| 4,208,745 A | | 6/1980 | Okita |
| 4,225,547 A | | 9/1980 | Okita |
| 4,279,245 A | | 7/1981 | Takagi et al. |
| 4,280,500 A | | 7/1981 | Ono |
| 4,332,035 A | | 6/1982 | Mano |
| 4,441,215 A | | 4/1984 | Kaster |
| 4,550,447 A | | 11/1985 | Seiler, Jr. et al. |
| 4,605,406 A | | 8/1986 | Cahalan et al. |
| 4,613,544 A | | 9/1986 | Burleigh |
| 4,619,641 A | | 10/1986 | Schanzer |
| 4,687,482 A | | 8/1987 | Hanson |
| 4,718,907 A | | 1/1988 | Karwoski et al. |
| 4,728,328 A | | 3/1988 | Hughes et al. |
| 4,729,766 A | | 3/1988 | Bergentz et al. |
| 4,731,073 A | | 3/1988 | Robinson |
| 4,743,252 A | | 5/1988 | Martin. Jr. et al. |
| 4,804,381 A | | 2/1989 | Turina et al. |
| 4,816,339 A | | 3/1989 | Tu et al. |
| 4,850,999 A | | 7/1989 | Planck |
| 4,877,661 A | | 10/1989 | House et al. |
| 4,955,899 A | | 9/1990 | Della Corna et al. |
| 4,973,609 A | | 11/1990 | Browne |
| 5,026,513 A | * | 6/1991 | House et al. ............... 26/167 |
| 5,064,593 A | | 11/1991 | Tamaru et al. |
| 5,100,422 A | | 3/1992 | Berguer et al. |
| 5,152,782 A | | 10/1992 | Kowligi et al. |
| 5,246,451 A | | 9/1993 | Trescony et al. |
| 5,246,752 A | | 9/1993 | Raczkowski |
| 5,433,909 A | | 7/1995 | Martakos et al. |
| 5,453,235 A | | 9/1995 | Calcote et al. |
| 5,476,589 A | | 12/1995 | Bacino |
| 5,529,820 A | | 6/1996 | Nomi et al. |
| 5,620,763 A | | 4/1997 | House et al. |
| 5,718,973 A | | 2/1998 | Lewis et al. |
| 5,735,892 A | | 4/1998 | Myers et al. |
| 5,747,128 A | | 5/1998 | Campbell et al. |
| 5,782,912 A | | 7/1998 | Brauker et al. |
| 5,800,529 A | | 9/1998 | Brauker et al. |
| 5,824,050 A | | 10/1998 | Karwoski et al. |
| 5,866,217 A | | 2/1999 | Stenoien et al. |
| 5,873,906 A | * | 2/1999 | Lau et al. ................... 623/1 |
| 5,882,354 A | | 3/1999 | Brauker et al. |
| 5,928,279 A | * | 7/1999 | Shannon et al. ............ 623/1 |

OTHER PUBLICATIONS

Eldrup–Jorgensen J et al. Evaluation of arterial prostheses in a baboon ex vivo shunt: The effect of graft material and flow on platelet deposition. American Journal of Surgery 1985; 150:185–190.

Kito H, Matsuda T. Biocompatible coatings for luminal and outer surfaces of small–caliber artificial grafts. Journal of Biomedical Materials Research 1996; 30:321–330.

Okoshi T. et al. In Vivo Evaluation of Porous Versus Skinned Polyurethane–Polydimethylsiloxane Small Diameter Vascular Grafts. ASAIO Transactions 1991; 37:M480–481.

Golden MA et al. Healing of polytetrafluoroethylene arterial grafts is influenced by graft porosity. J Vasc Surg 1990;11:838–45.

Lumsden AB et al. Nonporous silicon polymer coating of expanded polytetrafluoroethylene grafts reduces graft neointimal hyperplasia in dog and baboon models. J Vasc Surg 1996;24:825–33.

Okoshi T. New Concept of Microporous Structure in Small Diameter Vascular Protheses. Artificial Organs 1995;18(1)27–31.

Kito H et al. Differentiated Biocompatible Design of Luminal and Outer Graft Surfaces. ASAIO Journal 1993;39:M506–M511.

Brewster DC. Prosthetic Grafts. In: *Vascular Surgery,* ed. Rutherford RB. Philadelphia: W.B.Saunders Company 1995; 492–521.

Siedlecki CA, Marchant RE. Atomic force microscopy for characterization of the biomaterial interface. Biomaterials 1998; 19:441–454.

Snyder RW, Botzko KM. Woven, Knitted, and Externally Supported Dacron Vascular Prostheses. In: *Biologic and Synthetic Vascular Prostheses,* ed. Stanley JC. New York: Grune & Stratton, Inc. 1982;485–494.

Wesolowski SA et al. Porosity: primary determinant of ultimate fate of synthetic vascular grafts. Surgery 1961;50(1)91–96.

Yuan JG et al. The Effect of Nonporous PTFE–Covered Stents on Intimal Hyperplasia Following Balloon Arterial Injury in Minipigs. J Endovasc Surg 1998;5:349–359.

Yeh YS. Blood compatibility of Surfaces modified by plasma polymerization. Journal of Biomed Mater Res 1988;22:795–818.

\* cited by examiner

VASCULAR GRAFT WITH IMPROVED FLOW SURFACES

FIELD OF THE INVENTION

The present invention relates to the field of vascular grafts typically used to replace, line or otherwise repair living blood vessels or other body conduits.

BACKGROUND

The first effective vascular surgery reported in the literature was the work of T. Gluck who described in 1898 his placement of a vein graft in the carotid artery of a patient in 1894. Carrel and Guthrie reported in 1908 that they had successfully grafted a segment of a dog's vena cava, previously preserved in formalin, into a carotid artery. Guthrie prophetically concluded that these graft segments did not maintain the viability of living tissue but simply served as a conduit for blood and provided a possible scaffold for the ingrowth of cells. Carrel subsequently and unsuccessfully attempted to use tubes of glass and metal as vascular grafts.

Following the discovery by Voorhees that a loose silk thread lying within the right ventricle of a dog's heart became coated with an endothelial-like substance, it was proposed that a vascular substitute might be made of such threads. Vorhees et al. described in 1952 the use of short lengths of tubes made from Vinyon "N" cloth as replacements for aortic segments in dogs. In 1954, Voorhees and Blakemore described the replacement of 17 abdominal aneurysms and a popliteal aneurysm with synthetic tubes. Years of additional work by vascular surgeons building on this beginning led to the understanding that while conventional synthetic grafts of materials such as polyethylene terephthalate (PET) worked well in large diameter applications (for example, those involving repair of aortic aneurysms), their patency decreased with decreasing diameters. Darling and Linton in 1972 reported that eight-year PET implants in the leg had patency rates of about 10% in comparison to reversed saphenous vein patency rates of about 65–70%.

R. W. Gore invented porous expanded polytetrafluoroethylene (ePTFE) in 1969. He taught in U.S. Pat. Nos. 3,953,566 and 4,187,390 that polytetrafluoroethylene (PTFE) paste extrudate, following removal of the extrusion lubricant, could be rapidly stretched at a temperature below the crystalline melt point of PTFE to create the resulting porous microstructure of nodes interconnected by fibrils. During 1972, Soyer et al. reported using ePTFE tubes as venous replacements in pigs. Matsumoto et al. in 1973 described the use of ePTFE tubes as femoral artery replacements in dogs. In 1976, Campbell et al. first reported the use of ePTFE as a vascular substitute in humans. With further development to ensure adequate mechanical strength, these grafts soon became the standard for small diameter synthetic grafts. Even so, it was recognized that these improved synthetics sometimes did not perform equally as well as autologous saphenous vein grafts. It was noted that synthetic grafts, both PET and ePTFE, generally did not endothelialize beyond 1 or 2 cm from each anastomosis. The primary focus of further work on improved synthetic grafts since then has involved attempts to improve endothelialization of graft luminal surfaces. With regard to ePTFE grafts, this work frequently entailed methods of modifying the surface energy of the graft luminal surfaces to render the hydrophobic PTFE material much more hydrophilic. Conversely, woven PET grafts have been provided with luminal surface coatings of plasma-applied tetrafluoroethylene (TFE) monomer gas as taught by U.S. Pat. No. 4,718,907 to Karwoski et al.

Porosity has long been recognized to be a fundamental characteristic which affects the patency of synthetic vascular grafts; see, for example, the pioneering paper by Wesolowski et al., entitled "Porosity: primary determinant of ultimate fate of synthetic vascular grafts" (Suraerv, Vol. 50, No. 1 (July, 1961)). Accordingly, a great deal of the research into ePTFE grafts focused on efforts to optimize the mean fibril length of such grafts. While it has generally been concluded that these grafts were required to have a mean fibril length of at least 5–6 microns and no more than about 90 microns, the data reported in the literature remain inconsistent. See, e.g., Golden et al., "Healing of polytetrafluoroethylene arterial grafts is influenced by graft porosity," *J. Vasc. Surg.*, pp. 838–845 (June, 1990); also, Branson et al., "Expanded Polytetrafluoroethylene as a Microvascular Graft: A Study of Four Fibril Lengths," *Plastic and Reconstructive Surgery*, Vol. 76, No. 5, pp. 754–763 (November 1985). Commercially available ePTFE grafts typically have a mean fibril length at the luminal surface in the range of about 15–30 microns.

Various ePTFE tubes are described in the patent literature which have different mean fibril lengths on the luminal surface than elsewhere on the tube or which otherwise have at least two differing microstructures within the structure of the tube. They may differ in mean fibril length, directional orientation of the fibrils, or both.

U.S. Pat. Nos. 4,082,893 and 4,208,745 to Okita and 4,332,035 to Mano describe ePTFE tubes, intended for use as vascular grafts, which have been exposed to heat above the crystalline melt temperature of PTFE at their outer surface for a period of time adequate to cause modification of the exterior surface with the result that the microstructure at the exterior surface of the tube becomes coarser as a result of coalescing together of the components of the microstructure, and oriented radially rather than longitudinally. U.S. Pat. No. 4,822,361 to Okita et al. describes that this same type of tube may be optionally impregnated with various resorbable materials including collagen, albumin, chitosan and heparin.

U.S. Pat. No. 4,225,547 to Okita and U.S. Pat. No. 4,743,480 to Campbell et al. describe different methods of orienting the microstructure of ePTFE tubes in different directions at the inner and outer surfaces of the tubes. The tubes are also intended to be used as vascular grafts.

U.S. Pat. No. 4,550,447 to Seiler et al. teaches modification of tubular PTFE extrudate by scoring through a portion of the exterior wall prior to removal of the extrusion lubricant and stretching below the melt temperature, with the result being the creation of a denser, exterior ribbed structure integrally formed with the remainder of the tube. The tube is described as an exteriorly reinforced vascular graft.

Various patents teach coextrusion methods whereby different microstructures may be created in different, concentrically-arranged parts of the wall of ePTFE tubes. Different PTFE or other fluoropolymer resins may be concentrically coextruded to result in the differing microstructures. Likewise other materials such as siloxanes may be included in one or more of the coextruded layers. These patents include U.S. Pat. No. 4,816,339 to Tu et al., U.S. Pat. No. 4,973,609 to Browne, U.S. Pat. No. 5,064,593 to Tamaru et al., and U.S. Pat. No. 5,453,235 to Calcote et al. All of these teach the construction of ePTFE vascular grafts.

Still other patents teach the construction of ePTFE tubes having changing or alternating regions of different porosity along the length of the tube made by making radially oriented segments which differ in porosity between adjacent segments. U.S. Pat. No. 5,433,909 to Martakos et al. teaches a tubular ePTFE vascular graft made having narrow, alternating ring-shaped segments of porous ePTFE and non-porous PTFE. U.S. Pat. No. 5,747128 to Campbell et al. describes an ePTFE vascular graft having alternating ring-shaped segments of more and less dense ePTFE. This graft may be made to be circumferentially distensible to larger diameters, in which form it is useful as an intraluminal graft.

Various patents describe the modification of the luminal surfaces of ePTFE vascular grafts. For example, U.S. Pat. No. 5,246,451 to Trescony et al. teaches modification of ePTFE vascular graft luminal surfaces by gas plasma deposition of fluoropolymer coatings followed by binding of a protein to the modified luminal surface. Optionally, the resulting luminal surface is seeded with endothelial cells. European Patent EP 0 790 042 describes an ePTFE vascular graft wherein the luminal surface is modified to become hydrophilic followed by the immobilization of a tissue-inducting substance onto the surface.

With regard to ePTFE vascular grafts of relatively small mean fibril length, U.S. Pat. No. 4,177,334 to Okita teaches a method of making such a tube which also has a relatively high porosity.

Other patents teach the manufacture of different types of tubular ePTFE forms intended for applications other than vascular grafts. U.S. Pat. No. 4,279,245 to Takagi et al., U.S. Pat. No. 5,529,820 to Nomi et al. and U.S. Pat. No. 5,789,047 to Sasaki et al. describe various ePTFE tubes for use as endoscope tubes wherein at least the luminal surface of the ePTFE tube is made non-porous by filling or coating with siloxanes or fluoropolymers. Tubes of the type taught by Sasaki et al. having a luminal surface of PTFE are relatively smooth but are of very limited porosity, having a bulk density of about 1.55 g/cc (non-porous PTFE having a density of about 2.2 g/cc).

WO/90/06150 teaches the manufacture of a catheter tube wherein a length of non-porous PTFE tubing is provided with an integrally attached, porous ePTFE tip portion. U.S. Pat. No. 4,280,500 to Ono teaches the construction of a catheter introducer device having alternating, ring-shaped sections of non-porous PTFE and porous ePTFE.

The medical literature with respect to PTFE vascular grafts has generally focused on attempts to improve endothelial cell adherence to the luminal graft surfaces. From the voluminous vascular literature, occasional articles have discussed the need for less adherent surfaces. In particular, an article by Lumsden et al., "Non-porous silicone polymer coating of expanded polytetrafluoroethylene grafts reduces graft neointimal hyperplasia in dog and baboon models," *J. Vasc. Surg.*, Vol. 24,No. 5, pp. 825–33 (November 1996), describes the use of silicone to fully or partially coat the luminal surfaces of ePTFE vascular grafts thereby rendering the coated surface non-porous, after which the entire luminal surface of each graft was provided with a gas plasma coating of HFE/H2 monomer gas. In comparison to conventional ePTFE grafts utilized as femoral AV shunts in dogs, the coated grafts were found, following retrieval after 30 days, to have a lesser neointimal area at the venous anastomosis. The grafts used were of 6 mm inside diameter and about 2.5 cm length (i.e., a relatively large diameter graft in comparison to its quite short length, used in a high-flow application). The surface smoothness of the graft was limited by the surface morphology of the luminal surface of the ePTFE graft to which the silicone coating was applied. All grafts remained patent at the conclusion of both the dog and baboon studies. Related work is described in U.S. Pat. No. 4,687,482 to Hanson.

Other non-adherent coatings for use on the luminal surfaces of ePTFE grafts are described. Haimovich et al. describe that the use of chitosan and polyvinyl alcohol coatings may reduce platelet adhesion ("A New Method for Membrane Construction on ePTFE Vascular Grafts: Effect on Surface Morphology and Platelet Adhesion," *J. APPl. Polym. Sci.*, Vol. 63, pp.1393–1400, (1997)).

There remains a need for a small diameter vascular graft which offers improved patency in comparison to conventional available grafts. These grafts may be of particular value in small diameter applications, such as below-knee and coronary applications.

SUMMARY OF THE INVENTION

The present invention comprises an implantable device, preferably a vascular graft, having a unique blood contact surface that reduces or prevents the accumulation of occlusive blood components. This is achieved by providing an extremely smooth and substantially non-adherent luminal surface comprised of PTFE and most preferably porous expanded PTFE. The smooth luminal surface is provided in combination with a vascular graft which offers good handling and suture properties. The parameter of concern for smoothness of the luminal surface (surface values) of the present invention is Rq, which is the Root-Mean-Square roughness, defined as the geometric average of the roughness profile from the mean line measured in the sampling length, expressed in units of microns RMS. The luminal surface (i.e., the blood contacting surface) of the vascular graft of the present invention has a surface at least as smooth as about 1.80 microns RMS and more preferably as smooth as about 1.70 microns RMS, 1.60 microns RMS, 1.50 microns RMS, 1.40 microns RMS, 1.30 microns RMS, 1.20 microns RMS, 1.10 microns RMS, 1.00 microns RMS, 0.90 microns RMS, 0.80 microns RMS, 0.70 microns RMS, 0.60 microns RMS, 0.50 microns RMS, 0.40 microns RMS, 0.30 microns RMS and 0.25 RMS. Generally, greater smoothness is more preferred with values of about 1.00 microns RMS or smoother being seen as most preferred. A surface value of about 1.2 microns RMS or less appears to be particularly effective, with 0.6 microns RMS even more effective.

The smooth luminal PTFE surface is preferably the result of providing a smooth surface of small mean fibril length ePTFE material, in comparison to previously available PTFE grafts. The surface smoothness is believed to avoid or reduce adherence of occlusive blood components including blood platelets which are typically of about 2–4 micron diameter. The small pore size (generally characterized as the mean fibril length of the ePTFE microstructure) is preferably less than about 5 microns and more preferably less than about 3 microns. It is believed that the fibril length or pore size may be reduced until the smooth surface is non-porous, substantially non-porous or even entirely non-porous.

Reducing the pore size will in many cases result in reduced invasion of the pores of the graft by cells, and reduced diffusion rate of molecules through the graft wall according to Fick's Law. An entirely non-porous material would be completely resistant to passage to cells and molecules. The reduced penetration of cells and diffusion of molecules may have additional benefits in improving the function of vascular grafts.

This luminal surface lining is intended to provide a smooth surface to the vascular graft which is believed to be substantially non-adherent to occlusive blood components such as platelets, fibrin and thrombin, and impermeable to cells from the blood, thereby avoiding the formation of an occlusive coating which might ultimately increase in thickness over time and eventually result in graft occlusion. These increasingly thick coatings are known to be particularly problematic at the distal anastomoses of vascular grafts wherein it has been frequently documented that intimal hyperplasia occurring at that location will lead to occlusion and loss of graft patency. While these occlusive blood components are substantially prevented from sticking to the surface of the inventive graft, it is believed that various other blood components such as, for example, various proteins and/or endothelial cells, may still adhere to the surface without leading to a coating of the occlusive blood components responsible for a thickening neointima over time.

The smooth PTFE luminal surface of the graft of the present invention is also anticipated to benefit implant applications which do not involve blood contact. For example, the smooth PTFE luminal surfaces may augment implant performance by reducing bacterial adhesion for grafts used in applications such as biliary grafts and biliary stent grafts. The smooth surface may also offer benefit for applications in which it is considered desirable to avoid tissue fibrosis, such as intra-abdominal adhesion barriers.

While other grafts have been described heretofore having smooth surfaces, none offer such a surface combined with the benefits of a PTFE material. The use of PTFE provides the benefits of many years of experience with this highly biocompatible and extremely chemically inert material while avoiding the use of other materials which are likely to be less biocompatible.

The luminal surface of a graft of the present invention having a smooth, PTFE luminal surface may be demonstrated to provide PTFE at that luminal surface by various methods. XPS (x-ray photoelectron spectroscopy) is the preferred analytical method to identify the presence of PTFE at the luminal surface.

A "vascular graft" is herein defined as any conduit or portion thereof intended as a prosthetic device for conveying blood and therefore having a blood contacting (i.e., "luminal") surface. While it is intended primarily as a tubular form, the graft may also be a sheet material useful for patching portions of the circumference of living blood vessels (these materials are generally referred to as cardiovascular patches). Likewise, the term vascular graft includes intraluminal grafts for use within living blood vessels. The inventive grafts as such may also be used as a stent covering on the exterior, luminal or both surfaces of an implantable vascular stent. While it is not required that the smooth luminal surface graft of the present invention be bonded to a stent component, such a bond is preferred. Suitable methods of affixing the graft to a stent as a stent covering are described in U.S. Pat. No. 5,735,892 to Myers et al.

"Configured as a vascular graft" means that the completed device is suitable for use as a vascular graft, i.e., in addition to the smooth luminal surface, that the device is biocompatible, properly proportioned as to appropriate dimensions such as diameter, length and wall thickness, readily attachable to the intended living tissue such as by sutures, offers appropriate handling characteristics such as good flexibility, bending and resistance to kinking during bending, and is sterilizable. Accordingly, vascular grafts are tested for the intended use and labeled as such on packaging and in instructions for use.

Preferably, the substrate tube for the graft of the present invention is made from a conventional ePTFE tube having a microstructure of nodes interconnected by fibrils and a mean fibril length or internodal distance of about 5–90 microns, preferably between about 10–45 microns and most preferably between about 10–30 microns or even 15–30 microns. Tubes of mean fibril length between about 10–30 microns are generally referred to hereinafter as 30 micron mean fibril length ePTFE tubes if a specific mean fibril length value is not otherwise provided. Tubes of this type are used as substrate tubes onto which is provided a luminal surface covering of another ePTFE material which provides the extremely smooth luminal surface. Preferably, this luminal ePTFE surface layer is in the form of an expanded PTFE film which may be oriented with the primary direction of film stretching (the predominant direction of orientation of the fibrils and the higher strength direction of the film) substantially parallel to the direction of blood flow over the luminal surface, or substantially perpendicular to that direction, or at any angle or angles between parallel and perpendicular. The film is preferably a film made as taught by U.S. Pat. No. 5,476,589 to Bacino, incorporated by reference herein. This film is referred to hereinafter as '589 film.

These '589 films typically have fibrils oriented in all directions within the plane of the film. This is the result of film expansion in both longitudinal and transverse directions. The fibrils in the longitudinal direction typically have a significantly larger mean diameter than fibrils oriented in other directions. This orientation of the larger diameter fibrils can be used to determine the longitudinal direction of the film, which corresponds with the direction of higher strength. The fibrils can be conveniently viewed with the aid of light microscopy.

In addition to providing the extremely smooth and non-adherent PTFE luminal surface, the ePTFE tube having the luminal surface covering of ePTFE film has good mechanical strength properties including good hoop strength and resistance to dilatation resulting from exposure to blood pressure over long periods of time, is readily sutured (typically having a density of about 0.5–0.7 g/cc) and has good suture retention properties. The presence of the luminal film layer augments the mechanical strength properties of the inventive graft. The combination of the 10–30 micron fibril length substrate tube and the smooth luminal surface of ePTFE film also provides good flexibility and handling properties to the inventive graft.

The good handling properties are generally the result of providing a graft with a density of less than about 1.55, more preferably less than about 1.5, 1.4, 1.3, 1.2, 1.0, 0.9, 0.8, 0.7, 0.6 and 0.5, with the lower densities generally offering the best handling (ease of bending without kinking and ease of suturing) and thus being the most preferred. Density is considered to be the mass divided by the gross volume of the graft material and thus includes any void volume resulting from any porosity of the graft material (i.e., bulk density expressed in grams per $cm^3$). Because density is inversely proportional to porosity, it is a good indication of the amount of porosity or void space within the material. The density of non-porous PTFE is generally considered to be about 2.2 g/cc.

Density is to be determined for tubular vascular grafts by transversely cutting a representative 1 cm sample length of the graft with the result being a 1 cm long length of the graft tubing with ends cut perpendicular to the longitudinal axis of the graft tube. The tube is then cut through its wall thickness in the direction of its length (parallel to the longitudinal axis) and laid open with the result being a rectangular shape comprised of the graft material. The length and width are then measured along with the wall thickness to determine the bulk volume of the sample, after which the sample is precisely weighed to determine mass (weight). Wall thickness is measured by placing the sample between the pads of a Mitutoyo model no. 804-10 snap gauge having a part no. 7300 frame and gently easing the pads into contact with the opposing surfaces of the sample under the full force of the spring-driven snap gauge pads.

Grafts of the present invention as described above may have more than one component such as a first component of an ePTFE substrate tube and a second component of a layer of ePTFE film providing the luminal surface of the graft. The bulk density of such a graft thus includes the potentially different densities of the two or more components.

The vascular graft may be provided with any density within these described ranges in any combination with the previously described ranges of surface smoothness.

In an alternative embodiment the inventive graft may be made entirely from ePTFE film such as the '589 ePTFE film; examples of methods of making film-tubes are described in WO 95/05555.

Various embodiments of the vascular graft of the present invention may be made to be quite thin, particularly when made as film-tubes. While they may be made as thin as a single layer of this film (about 0.004 mm), they are preferably of greater thicknesses such as 0.013 mm, 0.05 mm, 0.08 mm, 0.1 mm, 0.2 mm and 0.5 mm, in order to allow for practical handling. The thin embodiments find particular utility as intraluminal grafts and as stent coverings. Thinness is a.desirable attribute in terms of the wall of the graft encroaching minimally into the available luminal space.

The graft may optionally be provided with rapid recovery or "stretch" characteristics as taught by U.S. Pat. Nos. 4,877,661; 5,026,513 and 5,308,664. Rapid recovery may be provided to ePTFE in different amounts such as more than about 6%, 8%, 10%, 15%, 20%, 22%, 25%, 30% or 50%.

While the preferred method of making the inventive vascular graft involves providing an ePTFE substrate tube with a smooth luminal surface of ePTFE film, it is recognized that there may be other ways of making such a graft.

BRIEF DESCRIPTION OF THE DRAWINGS

FIGS. 8A, 8B and 8C show respectively longitudinal cross sections of stents provided with coverings of the inventive vascular grafts, wherein FIG. 8A shows a covering provided on the luminal surface of a stent, FIG. 8B shows a covering provided on the exterior surface of a stent and FIG. 8C shows a covering on both the luminal and exterior surfaces of a stent.

DETAILED DESCRIPTION OF THE DRAWINGS

Figure 1:
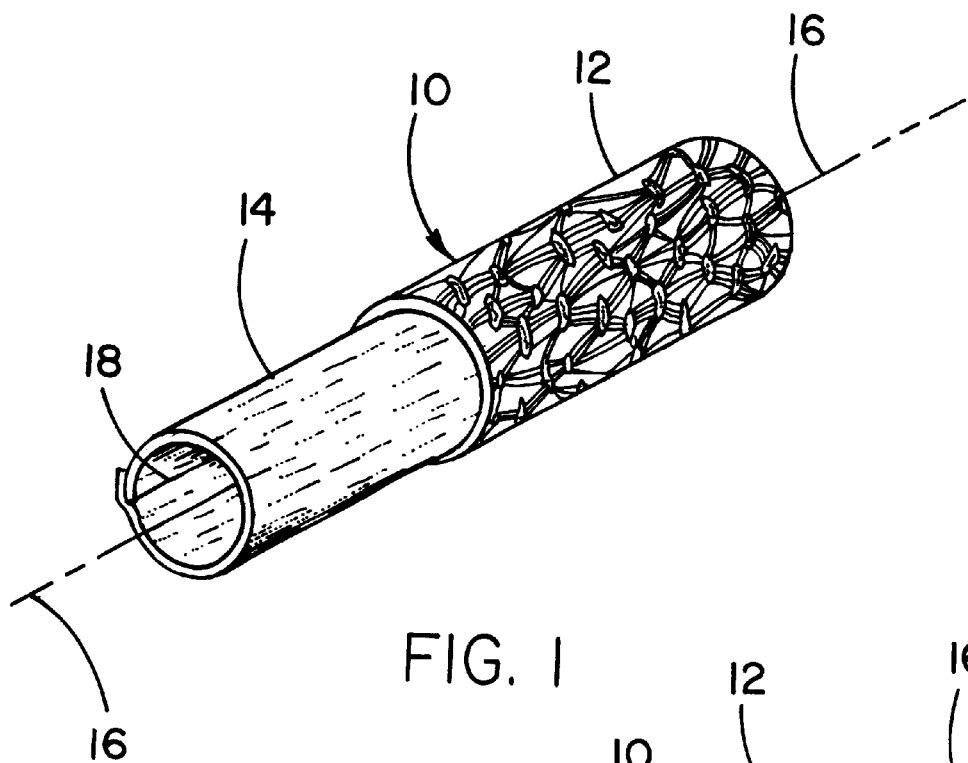
FIG. 1 is a cutaway isometric view of a vascular graft according to the present invention depicting schematically a longitudinally extruded and expanded tube of ePTFE provided with a luminal surface lining of one or more layers of an ePTFE film wherein the higher strength direction of the film is oriented parallel to the longitudinal axis of the tube.

FIG. 1 shows a cutaway isometric view of a vascular graft 10 of the present invention wherein a substrate tube 12, preferably of ePTFE, is provided with a luminal surface covering of an ePTFE film layer 14. The ePTFE substrate tube 12 is preferably a longitudinally extruded and expanded PTFE tube of between about 10–30 microns mean fibril length; it is anticipated that ePTFE tubes of other fibril lengths may be used as well. This tube 12 may be a relatively conventional ePTFE tube as used previously for commercially available vascular grafts, such as GORE-TEX® brand vascular grafts available from W. L. Gore & Associates, Flagstaff, Ariz. It provides the finished graft with good suture retention, flexibility and handling properties which surgeons are already familiar with.

A luminal surface lining 14 is provided within the substrate tube 12, wherein the liner 14 is preferably one or more layers of the '589 ePTFE film. Such films are preferably made by stretching in a primary direction (typically the length direction of the film and the higher strength direction of the film) with the result that the fibrils of the film microstructure (visible with the aid of magnification) have a predominant orientation in the direction of higher strength.

The ePTFE film luminal surface covering 14 is preferably provided by orienting the film so that the higher strength direction of orientation of the film is aligned to be substantially parallel to the longitudinal axis 16 of the tubular graft 10. The film is most easily applied in one or more layers to have an edge or seam 18 which is also substantially parallel to the longitudinal axis 16 and which extends between the ends of the graft.

Figure 1A:
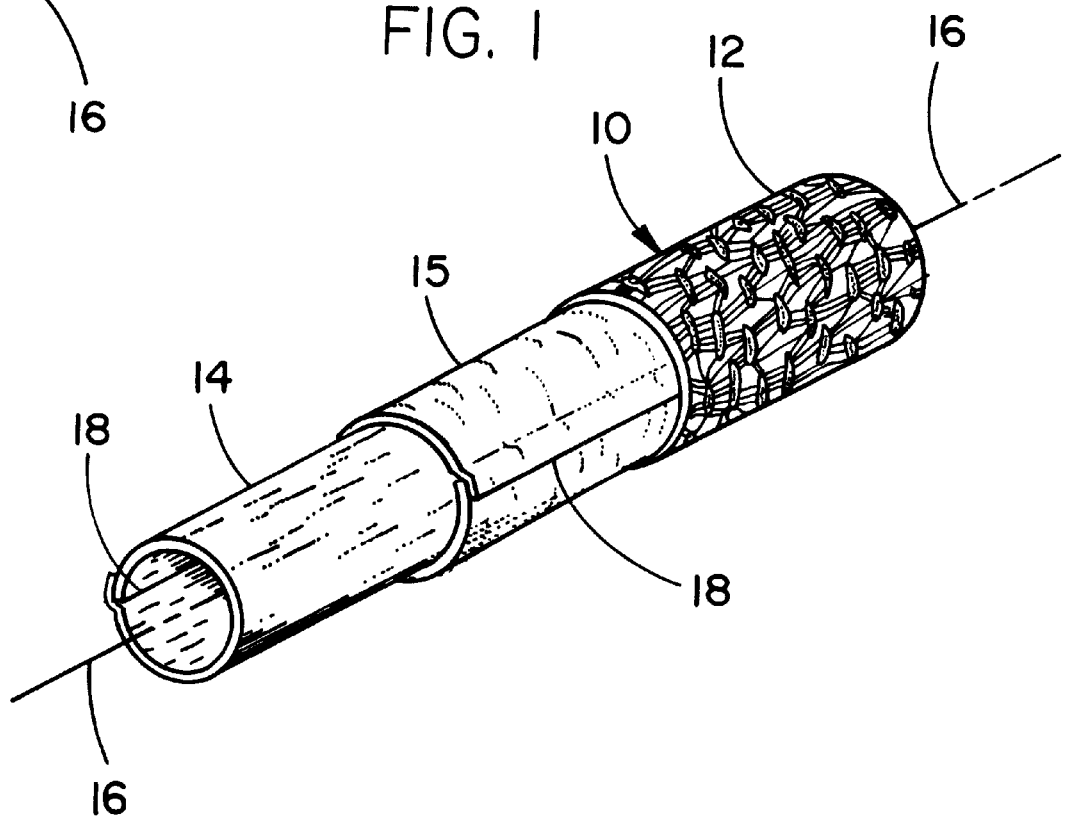
FIG. 1A is a cutaway isometric view of an inventive vascular graft similar to that of FIG. 1 having an added intermediate layer or layers of the same film used for the luminal surface wherein the higher strength direction of the film used as the intermediate layer(s) is oriented in a circumferential direction.

In a variation on this embodiment described by FIG. 1A, the graft 10 may be provided with one or more additional intermediate layers of film 15 of the same type as layer 14, except that the additional layer(s) 15 have the direction of higher strength oriented in a helical or circumferential direction with respect to the tubular graft 10. Such a layer 15 provides additional hoop strength and resultant additional resistance to dilatation.

Figure 2:
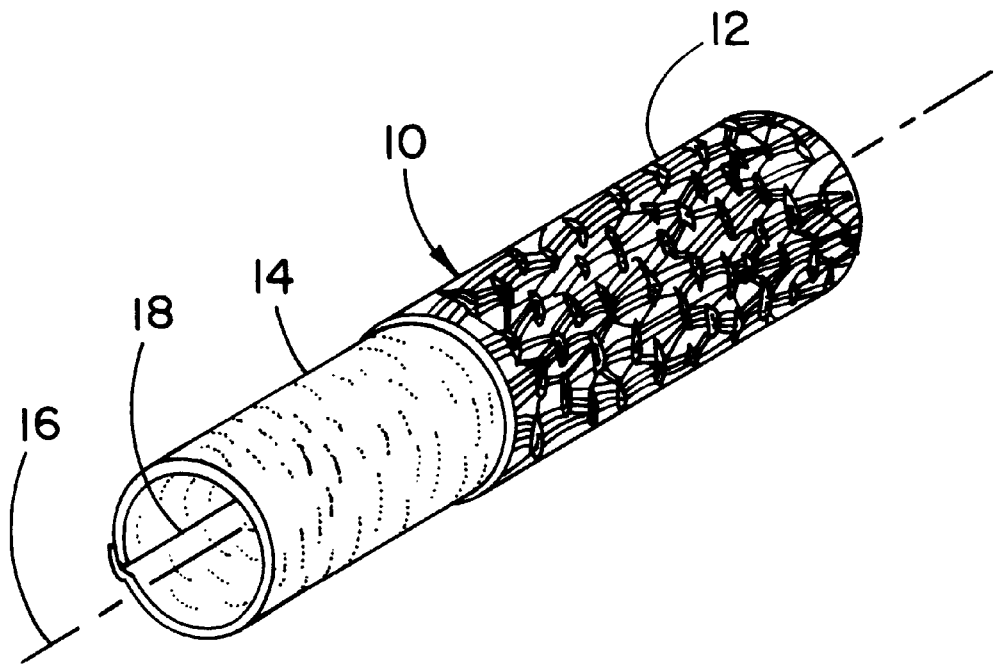
FIG. 2 is a cutaway isometric view of a vascular graft according to the present invention depicting schematically a longitudinally extruded and expanded tube of ePTFE provided with a luminal surface lining of one or more layers of an ePTFE film wherein the higher strength direction of the film is oriented circumferentially.

Alternatively, one or more layers of the film 14 at the luminal surface may be oriented with the higher strength direction of the film in a substantially circumferential direction as shown by FIG. 2. For this orientation, it is preferred that a sheet of ePTFE film be used for the luminal surface lining which is of adequate width to span the entire length of the graft. In this fashion the resulting edge or seam line 18 of the film can be aligned to be substantially parallel to the longitudinal axis 16 of the graft.

Figure 2A:
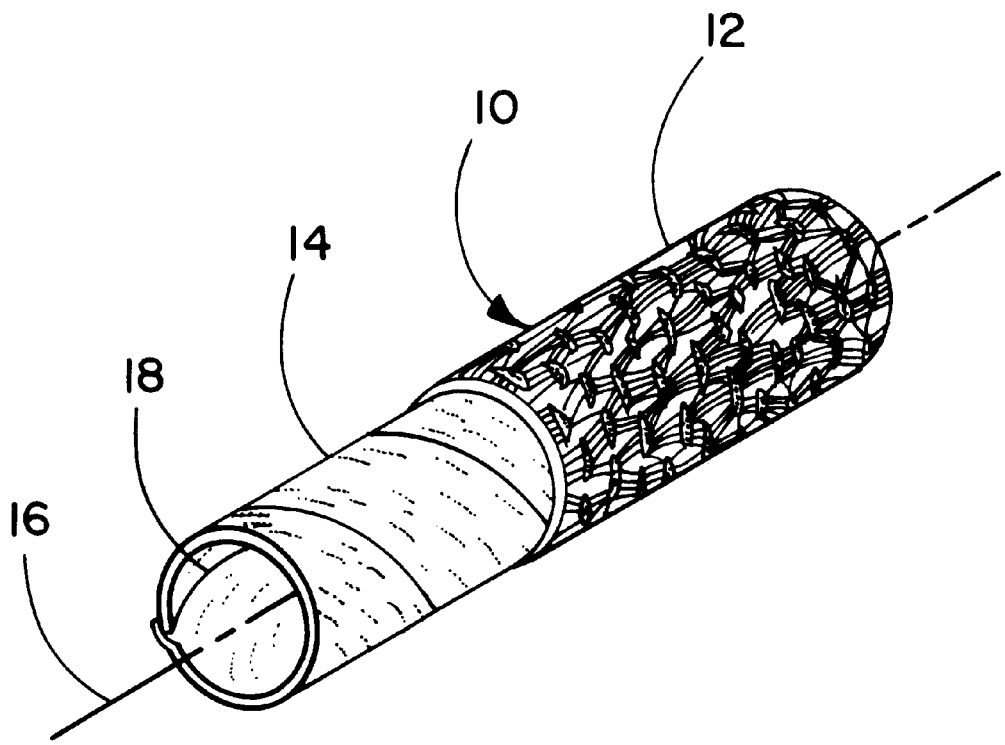
FIG. 2A is a cutaway isometric of an alternative embodiment with regard to that shown by FIG. 2 wherein the higher strength direction of orientation of the film is helical, provided in the form of a helical wrap of the film.

In a variation of this embodiment shown in FIG. 2A, the higher strength direction of the film 14 is provided in a helical orientation in the form of a helical wrapping of the film 14. The film applied to the luminal surface may thus be applied as a helical wrap of a narrower and longer length of tape cut from the ePTFE film, with adjacent edges of the helical winding overlapping. If made in this fashion, it is believed that it is preferred to implant the graft with the raised edges of the overlap at the trailing edge of the film with respect to the direction of blood flow, that is, with these edges directed distally (or downstream with respect to the direction of blood flow) rather than proximally.

As shown in FIGS. 1, 1A and 2, the graft is most easily made by wrapping a sheet of the film material over the surface of a mandrel with the film edge 18 oriented to be substantially parallel to the longitudinal axis 16 of the graft and the mandrel, and with the higher strength direction of the film oriented as desired. A suitable ePTFE tube 12 is then carefully fitted over the film layer(s) 14 or 15, after which the assembly is placed into an oven heated to above the crystalline melt temperature of PTFE (about 327° C.) for a time suitable to result in the thermal bonding of the film and tube.

Figure 3:
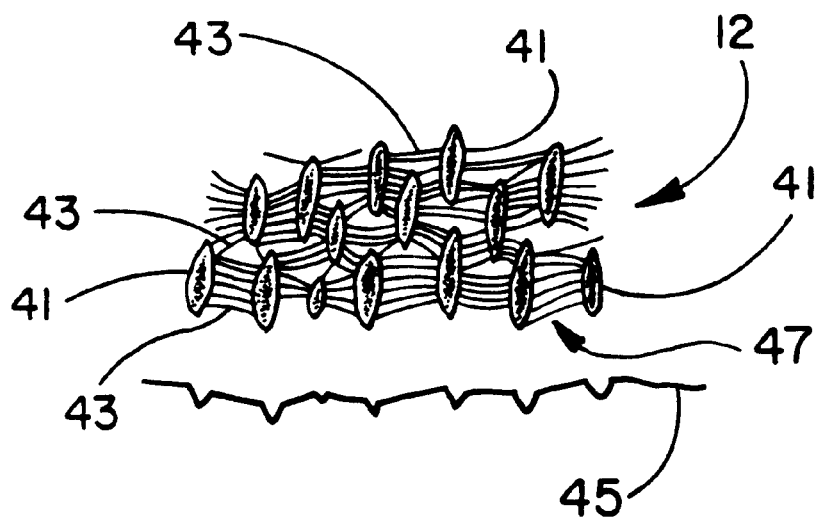
FIG. 3 is a schematic rendering of a longitudinal cross section of the upper wall of a conventional, prior art ePTFE vascular graft (including a longitudinal cross sectional view of the luminal surface of the graft) having a mean fibril length at the luminal surface of about between about 10–30 microns.

FIG. 3 illustrates in schematic fashion a longitudinal cross section of the upper wall of a conventional vascular graft of the prior art in the form of an ePTFE tube 12 having an approximate mean fibril length at the luminal surface 47 of between about 10–30 microns. The tube 12 is shown with its microstructure of nodes 41 interconnected by fine fibrils 43. It should be understood that the surface morphology presented to the flowing blood (comprised substantially of platelets of about 2–4 micron diameter) is relatively rough and irregular as represented by profile line 45 shown immediately below and parallel to the luminal surface 47. In reality, due to the three dimensional nature of the porous luminal surface and the relatively large effective pore size in comparison to blood platelets, the luminal surface morphology presented to the blood components is even more irregular than shown by profile line 45.

Figure 3A:
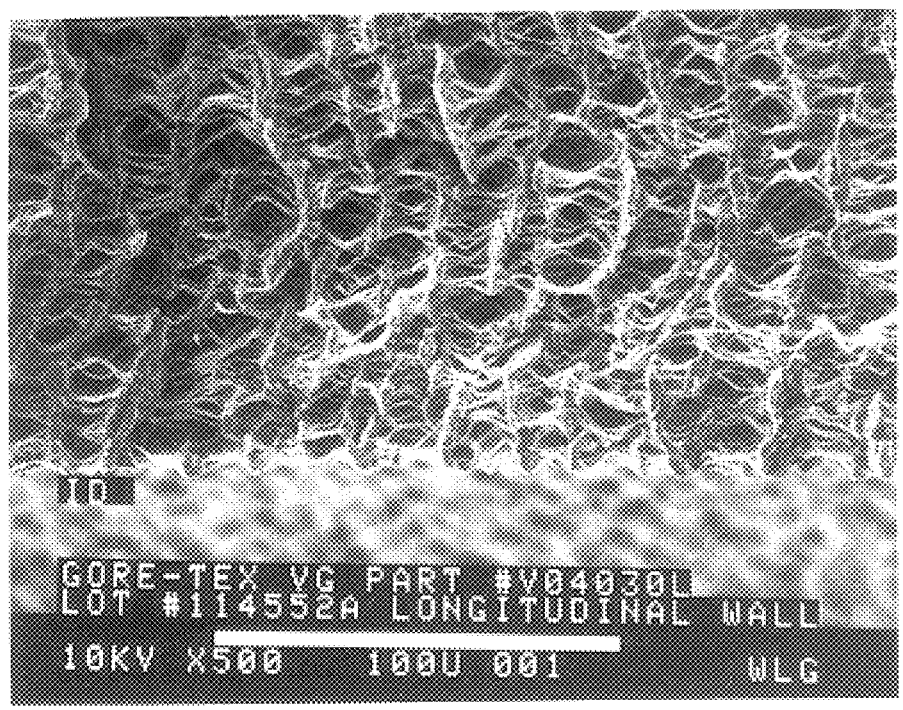
FIG. 3A is a photomicrograph (500×) of a longitudinal cross section of a sample of a commercially available ePTFE GORE-TEX® brand vascular graft, analogous to the schematic view of FIG. 3. The lower edge of the sample thus illustrates a longitudinal cross section of the luminal surface.

FIG. 3A is a photomicrograph (500×) of a longitudinal cross section of the upper wall of a sample of a commercially available ePTFE vascular graft (GORE-TEX® brand vascular graft, Part No. V04030L), analogous to the schematic view of FIG. 3. The lower edge of the sample thus describes a longitudinal cross section of the luminal surface.

Figure 4:
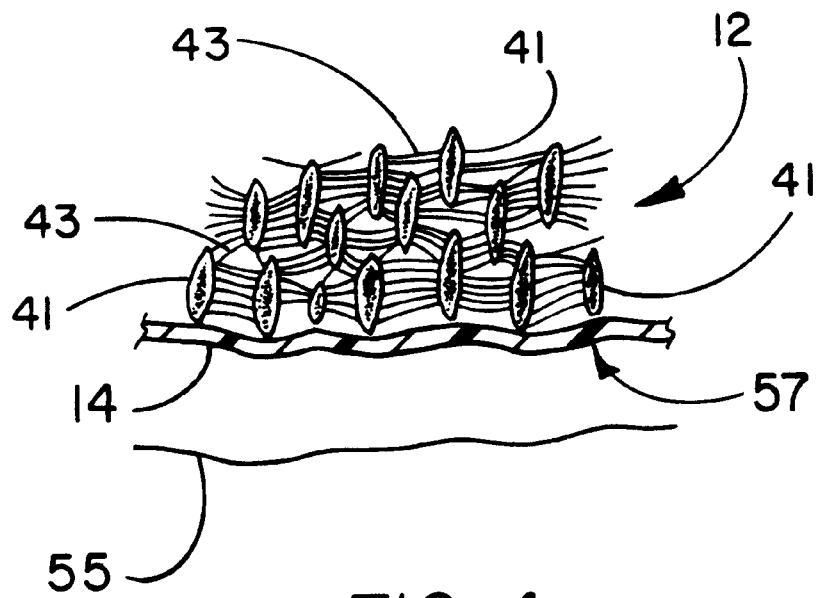
FIG. 4 is a schematic rendering of a longitudinal cross section the upper wall of an ePTFE vascular graft of the present invention (including a longitudinal cross sectional view of the luminal surface of the graft), wherein a substrate tube of ePTFE of between about 10–30 micron mean fibril length is provided with a smooth luminal surface of three layers of '589 ePTFE film.

FIG. 4 shows schematically a longitudinal section of the upper wall of a vascular graft, now in the form of a graft of the present invention, wherein an ePTFE tube 12 is provided with a luminal surface covering of the '589 ePTFE film 14. The morphology of the resulting luminal surface 57, as represented by the parallel profile line 55 shown suspended below luminal surface 57, is substantially smoother with respect to the blood components which will contact this surface in comparison to the surface 47 of FIG. 3. It is believed that such a smooth surface will substantially reduce or prevent adhesion of occlusive blood components and prevent the passage of cells through the film layer.

Figure 4A:
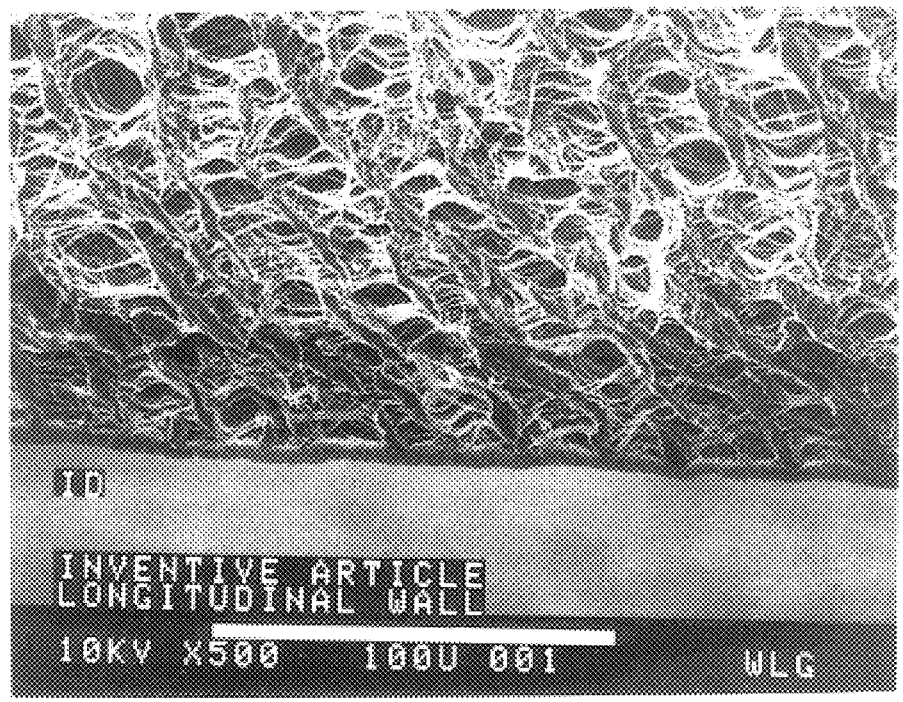
FIG. 4A is a photomicrograph (500×) of a longitudinal cross section of a sample of an ePTFE vascular graft of the present invention having smooth luminal surface resulting from the application of three layers of '589 ePTFE film to the luminal surface wherein the film has a mean fibril length of less than about 5 microns (analogous to the schematic view of FIG. 4). The lower edge of the sample thus illustrates a longitudinal cross section of the luminal surface.
Figure 4B:
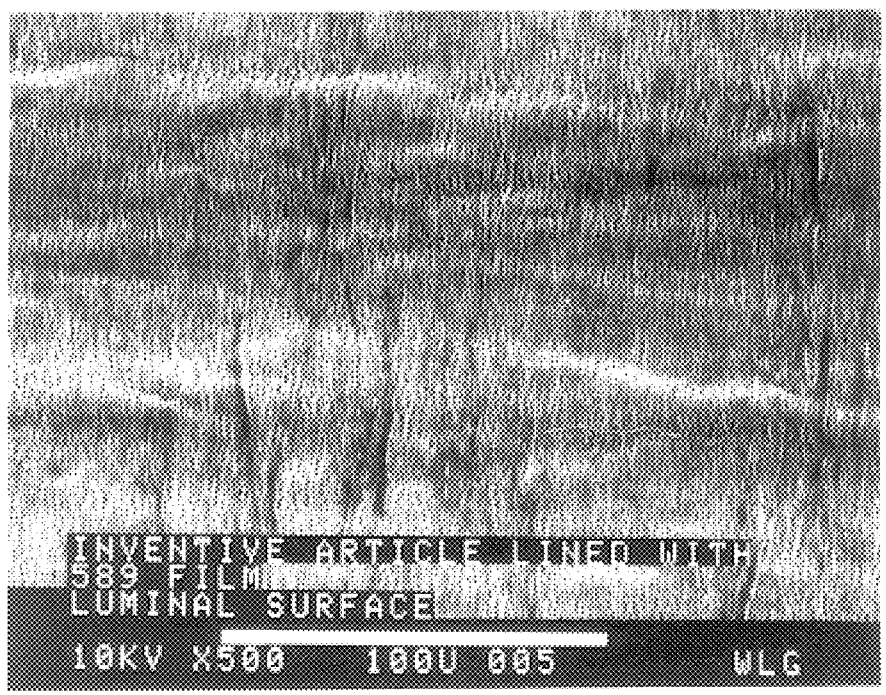
FIGS. 4B and 4C are photomicrographs (500× and 5000×, respectively) of the luminal surface of the graft of FIG. 4A.
Figure 4C:
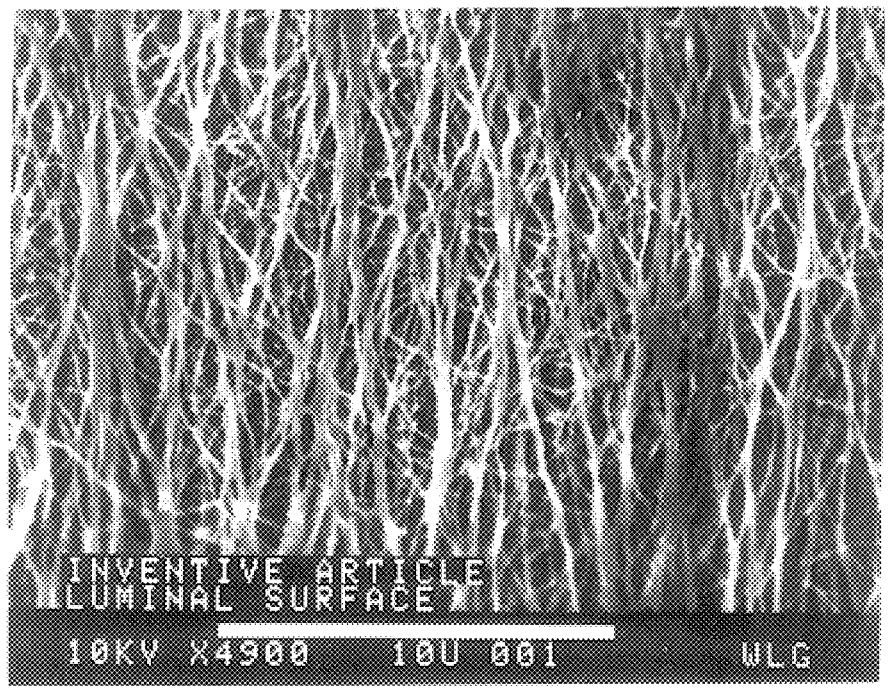

FIG. 4A is a photomicrograph (500×) of a longitudinal cross section of the upper wall of a sample of an ePTFE vascular graft of the present invention having smooth luminal surface resulting from the application of three layers of the '589 ePTFE film to the luminal surface (analogous to the schematic view of FIG. 4). The lower edge of the sample thus describes a longitudinal cross section of the luminal surface. FIGS. 4B and 4C (500× and 5000×, respectively) describe photomicrographs of the luminal surface the graft depicted in FIG. 4A.

Figure 5:
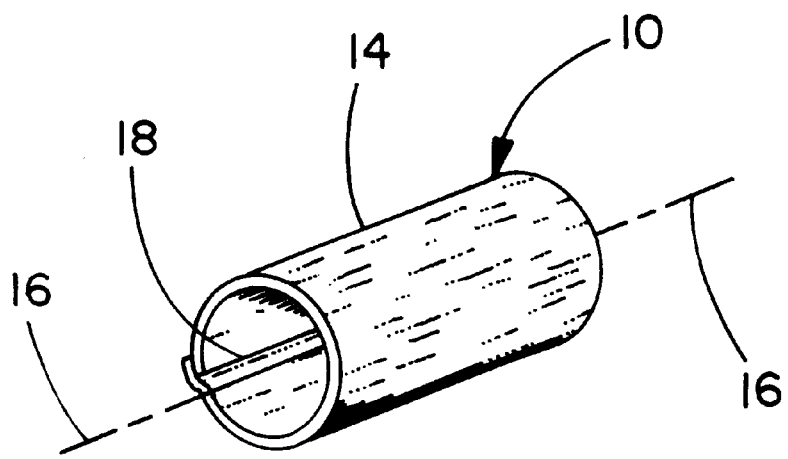
FIG. 5 is an isometric view of an alternative embodiment of the vascular graft of the present invention wherein the vascular graft comprises a tube of suitable ePTFE film, wherein the orientation of the higher strength direction of the film is parallel to the longitudinal axis of the tube.

In another alternative described by FIG. 5, the graft may comprise a tube of the above-described film (film-tube) without the overlying substrate tube wherein the film comprises not only the luminal surface of the tube but the entirety of the tube as well. Such a tube may be made in a similar fashion to that described above with the film wrapped around the surface of a suitable mandrel. The film may be wrapped with any desired orientation of the higher strength direction of the film and in any number of desired layers including only a single layer, having enough overlap at the edge of the film to allow joining by methods such as by heating briefly above the melt temperature of the film. These film-tubes may be used as intraluminal grafts for providing a new luminal surface for existing natural blood vessels (including both arteries and veins) and likewise may be used to provide a covering for stents by being joined to the exterior surface of a stent (thereby covering the interstices between adjacent stent structural components), the luminal surface of a stent or both exterior and luminal surfaces. The use of such a film-tube may be effective for various types of stents including self-expanding and balloon-expandable stents. The film covering may be joined to the stent by a variety of methods including those taught by U.S. Pat. No. 5,735,892 to Myers et al.

Figure 5A:
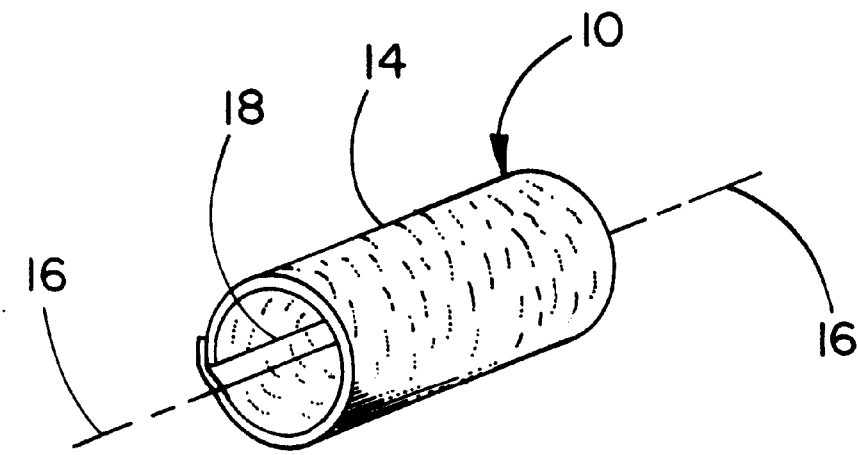
FIG. 5A is an isometric view of an alternative embodiment of the vascular graft of the present invention wherein the vascular graft comprises a tube of suitable ePTFE film, wherein the orientation of the higher strength direction of the film is circumferential

FIG. 5A illustrates an alternative embodiment to that of FIG. 5 wherein the orientation of the higher strength direction of the film is circumferential as opposed to the longitudinal orientation used in FIG. 5. As noted, the higher strength direction of the film may be oriented in any desired direction. Further, the film may be applied in different overlying layers wherein the different layers have different orientations of the higher strength direction of the film. For example, an inner layer may be used to create the luminal surface wherein that layer has a longitudinal oriention of the higher strength direction of the film, with an overlying outer layer wherein the orientation is circumferential or helical. Different helically oriented layers may be used with a first layer having a helical orientation in one direction and the other in the opposite direction (opposing helices). Still further, biaxially or multi-axially oriented films, that is, films having fibrils oriented in more than one or multiple directions and not having a predominant single higher strength direction, may also be used to create film-tubes. The primary criteria for purposes of the present invention is that the use of the film on the luminal surface results in an adequately smooth surface. Still further, any of these film-tube constructions may be used to provide a smooth luminal surface within a substrate tube.

Figure 5B:
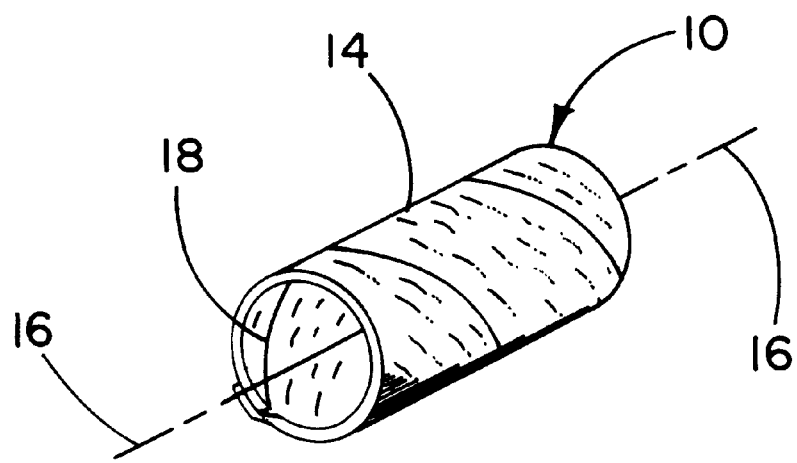
FIG. 5B is an isometric view of an alternative embodiment to that of FIG. 5A, wherein the orientation of the higher strength direction of the film is helical.

FIG. 5B is a perspective view of an alternative embodiment to that of FIG. 5A, wherein the orientation of the higher strength direction of the film is helical.

While FIGS. 5, 5A and 5B describe film-tubes incorporating a seamline wherein edges of the film overlap, it is anticipated that suitable film-tubes may also be made without seams by extrusion and subsequent expansion of tubular PTFE forms or by methods such as taught by U.S. Pat. No. 5,620,763. Such film-tubes (of either seamed or seamless construction) may be used to provide the necessary luminal surface of the above-described smoothness.

Figure 6:
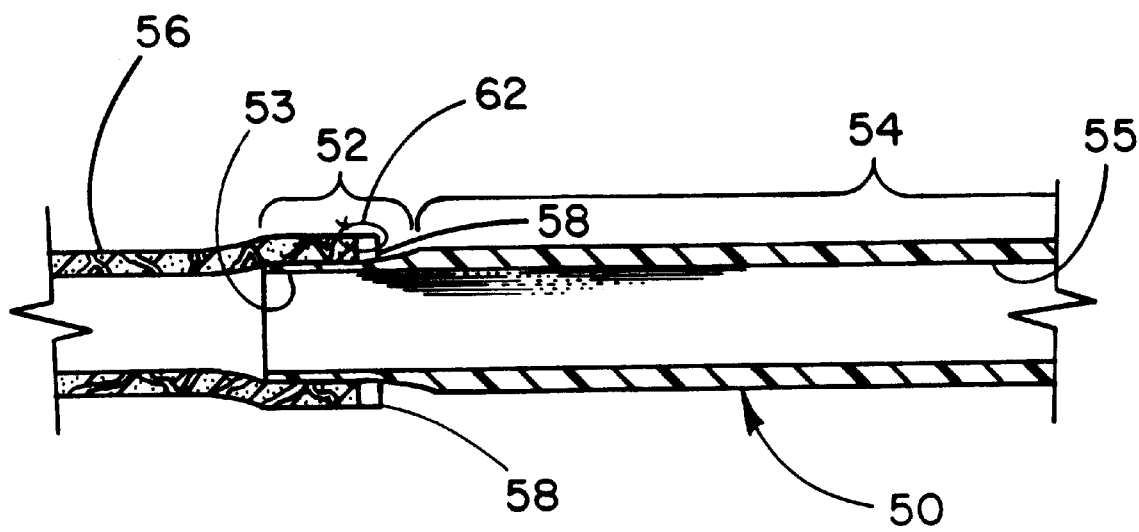
FIG. 6 is a longitudinal cross sectional view of an alternative vascular graft according to the present invention wherein the smooth PTFE luminal surface is provided only for a relatively short length at an end of the tube wherein the end is intended for use as a graft anastomosis.

In an alternative embodiment described by the longitudinal cross section of FIG. 6, a vascular graft 50 may be made having a smooth luminal surface 53 at only one or both ends 52 of the graft 50, in the region of the anastomosis of the graft 50 with a living vessel 56. The graft end 52 having the smooth luminal surface 53 may be of a relatively short length, such as about 0.5, 1.0, or 1.5 cm. The length 54 of the graft 50 between the two ends or adjacent to the one end 52 may be made with a more typical or conventional surface 55 similar to the luminal surface of commercially available ePTFE grafts having between about 10–30 micron fibril length microstructures. If the graft is made with a single end having a smooth luminal surface, that end is preferably implanted at the distal end of the vascular graft 50. Alternatively and more preferably, the entire length of the graft may be provided with the smooth luminal surface.

One method of making such a graft 50 begins with an ePTFE precursor tube which has been extruded and expanded by stretching as taught by U.S. Pat. Nos. 3,953, 566 and 4,187,390 to Gore, incorporated by reference herein. The tube is preferably a small diameter tube, having an inside diameter of 6 mm or less. Such a tube, for example, might have an inside diameter of about 3 mm, a wall thickness of about 0.5 mm and a node and fibril microstructure having a mean fibril length between about 10–30 microns.

A vascular graft made according to this procedure may optionally be further modified by having a suture ring 58 fitted to the exterior surface of the graft 50 near the end 52. Such a suture ring may allow completion of a sutured anastomosis without requiring that the sutures penetrate entirely through the wall of the vascular graft in conventional fashion (i.e., with portions of the length of suture extending into the graft lumen and into the blood flow).

FIG. 6 also illustrates a vascular graft 50 having an end 52 with a smooth luminal surface made according to the above-described procedure and further modified with such a suture ring 58. The smooth end 52 of the graft 50 is shown connected to a living blood vessel 56 via the suture ring 58 and suture 62. The transected end of the living blood vessel 56 is fitted over the exterior surface of the end 52 of the vascular graft 50 until it contacts the suture ring 58. The end of blood vessel 56 is then affixed to the suture ring 58 via the indicated suture 62. While the anastomosis described by FIG. 6 may be either a proximal or distal anastomosis, this technique is believed to most benefit a distal anastomosis. It is believed to avoid occlusion by blood components in the anastomotic region by both offering the anti-thrombotic, smooth luminal surface 53 of the smooth graft end 52 adjacent to the living blood vessel 56, while simultaneously avoiding sutures and large suture holes entirely through the thickness of the graft wall and extending into the bloodflow.

The suture ring 58 must be of a material suitable for penetration by suture needles and sutures and is therefore preferably of the same material as the graft. A suture ring of the type shown by FIG. 6 may be made by simply cutting transverse, ring-shaped slices from an end of a length of vascular graft tubing which has an inside diameter slightly smaller than the outside diameter of the graft over the exterior surface of which it is intended to be fitted. The ring is most easily and precisely fitted over the exterior surface of the graft by first inserting a snugly-fitting mandrel into the end of the graft in order to support the graft during the fitting process. In the case of ePTFE grafts, a suture ring of ePTFE is preferably joined to the exterior surface of the ePTFE graft with a biocompatible adhesive such as fluorinated ethylene propylene (FEP). FEP may, for example, be used as a strip of thin film (Daikin 0.0005 inch thick (0.0125 mm) FEP film, available from Norton Performance Plastics, Inc., Wayne, N.J.) fitted between the suture ring and exterior graft surface with bonding effected by the application of heat adequate to cause melting of the FEP. This allows it to penetrate into the adjacent porous microstructure of the ePTFE. Other biocompatible adhesives or other joining or forming methods may also be used to create such a suture ring.

Figure 6A:
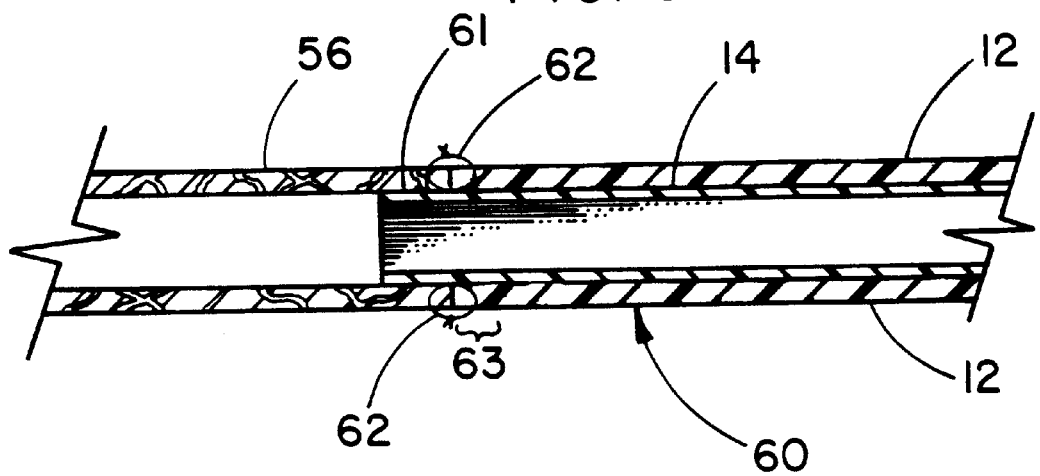
FIG. 6A is a longitudinal cross section of an alternative vascular graft of the present invention wherein a luminal surface lining of ePTFE film extends beyond an end of the substrate tube to which the lining is affixed.

FIG. 6A is a longitudinal cross section of an alternative vascular graft of the present invention wherein a luminal surface lining of ePTFE film 14 extends beyond an end of the substrate tube 12 to which the lining is affixed. The result is similar to the graft of FIG. 6 to the extent that at a distal anastomosis the extended luminal surface film lining 61 at implantation extends beyond the anastomosis of the substrate tube 12 with the living vessel 56. While sutures 62 may extend through the wall of the living vessel 56 and into the lumen of the living vessel 56, these sutures 62 and resulting suture holes which would otherwise be exposed to the blood flow are now allowed to be covered by the extended luminal surface lining 61of film 14. This is made further possible by having a short length 63 (about 0.5 cm) of the luminal surface film lining 14 at the very end of the substrate tube 12 (and immediately adjacent to the extended portion of the film lining 61) which is not affixed to the inner surface of the substrate tube 12. This allows the film in this region 63 to be held slightly away from the substrate tube 12 during suturing of the substrate tube 12 to the transected end of the blood vessel 56, so that penetration of the sutures through the film 14 is avoided.

Figure 7:
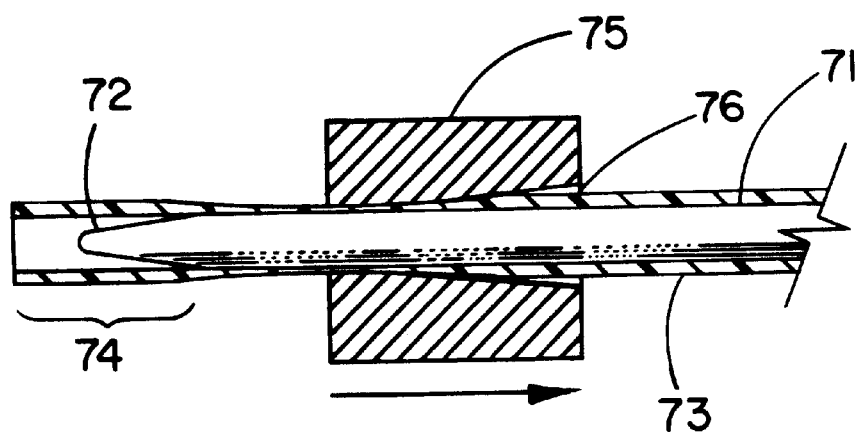
FIG. 7 is a longitudinal cross sectional view of a process of making the densified end of the inventive graft described by FIG. 6.

One method of making the graft of FIG. 6 is described in the longitudinal cross sectional view of FIG. 7. One end of the precursor tube 73 is fitted over an end of a stainless steel mandrel 71 having about a 5 degree taper 72 on that end of the mandrel and having a maximum diameter equal to or slightly larger than the inside diameter of the precursor tube 73. The remaining free length 74 of the precursor tube 73 (the portion of the tube not fitted over the mandrel) is inserted into the smooth, tapered lumen 76 of a tubular die 75, which is preferably a stainless steel die. The die 75 is of about 1–1.5 cm length and of a minimum inside diameter equal to the inside diameter of the tube plus twice a desired percentage of the wall thickness of the die-compressed end of the tube (e.g., twice 35% of the wall thickness of the precursor tube). The free length 74 of the precursor tube 73 is pulled entirely through the die 75 followed by the portion of the tube fitted over the tapered mandrel 71. As the mandrel 71 and tube 73 pass through the die 75, the increasing diameter of the tapered mandrel 71 and the tapered lumen of the die 75 result in compression of the wall of the precursor tube 73 between the mandrel 71 and die 75 with the wall thickness ultimately being reduced to the clearance between the largest diameter of the mandrel 71 and the minimum inside diameter of the tapered lumen 76 of the die 75. The reduced wall thickness (reduced to typically about 20 to 50% of that of the precursor tube) in the portion of tube 73 which has been compressed between the mandrel 71 and the tapered lumen 76 of die 75 results in a smooth, luminal surface of effectively increased density and reduced porosity at the end of the graft. The length of the densified section (and the associated smooth luminal surface and reduced thickness wall) may be made to or cut to any desired length. This procedure may be performed at room temperature or may be done in a heated environment to reduce the axial force necessary to pass the mandrel and tube through the die.

Figure 8A:
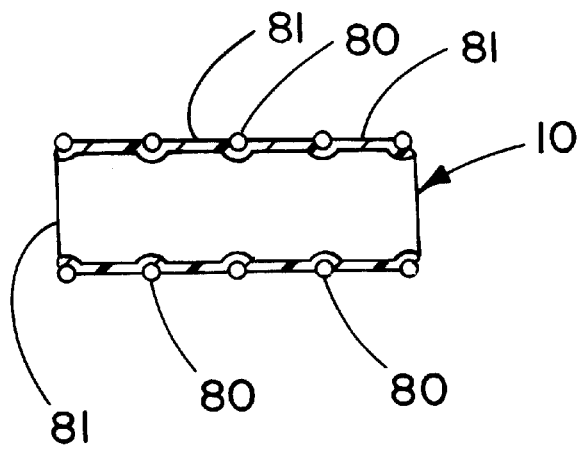
Figure 8B:
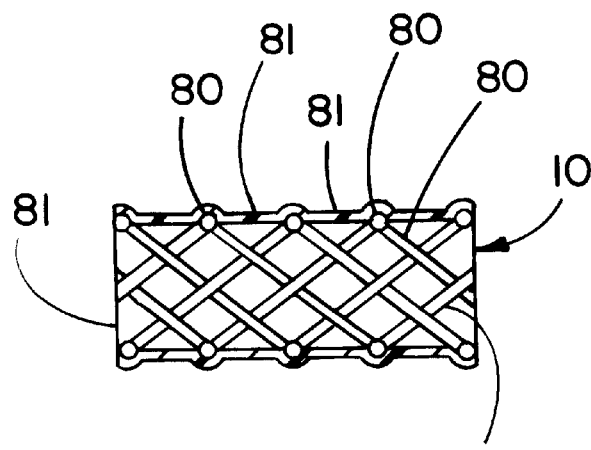
Figure 8C:
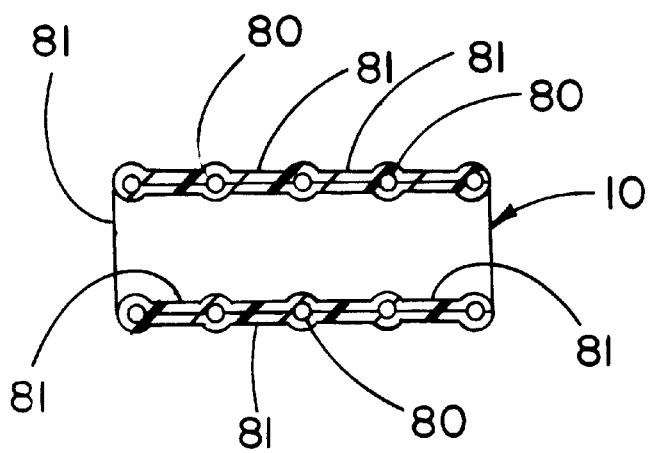

FIGS. 8A, 8B and 8C show respectively longitudinal cross sections of stents 80 provided with coverings 81 of the inventive vascular grafts 10 having smooth luminal surfaces, wherein FIG. 8A shows a covering 81 provided on the luminal surface of a stent 80. FIG. 8B shows a covering 81 provided on the exterior surface of a stent 80 and FIG. 8C shows a covering on both the luminal and exterior surfaces of a stent 80. The stents may be stents of any type which are circumferentially distensible from a smaller circumference at which dimension the stent is inserted into the vascular system, to a larger circumference at which the stent is deployed against the luminal surface of the body conduit (which is likely a vascular body conduit but is not limited to vascular body conduits). The stent types particularly include balloon expandable stents and self expanding stents and most particularly self expanding stents of shape-memory or super-elastic materials such as nitinol.

Figure 9:
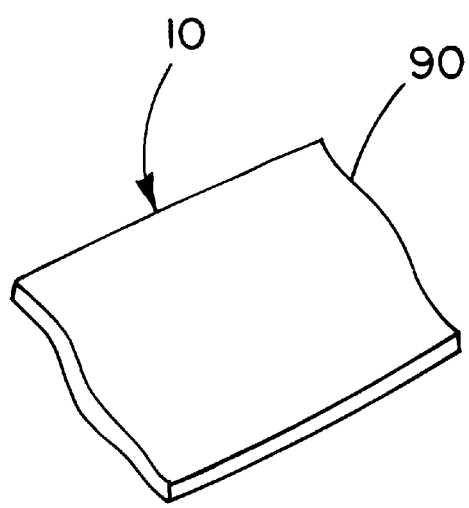
FIG. 9 shows a graft of the present invention which is a biocompatible sheet material intended for the repair of body tissues including vascular conduits.

FIG. 9 shows a graft 10 of the present invention which is a biocompatible sheet material 90 intended for the repair of body tissues. It is most preferably a vascular graft intended as a cardiovascular patch material. As such it is apparent that the sheet may be cut to any desired shape as necessary for the repair of any portion of the surface of a vascular body conduit such as an artery or vein. Likewise, because of its non-adherent character, the sheet may be effectively used for non-vascular repairs such as wall defects generally and particularly hernia repairs. At least one of the major surfaces of the sheet will be smooth as described herein and both (opposing) major surfaces may be smooth. One method of making such a smooth sheet is to laminate to one major surface one or more layers of the '589 ePTFE film; methods of lamination of ePTFE materials are known in the art.

Any of the above-described ePTFE vascular grafts may be provided with an external layer of helically-wrapped reinforcing film for additional hoop strength and resistance to dilatation. Such a film should preferably have an approximate fibril length of about 30–50 microns to allow for the ingrowth of adjacent tissue into the external surface of the graft. In a similar fashion, other layers may be added to the above-described constructions as long as the graft is provided with the smooth PTFE luminal surface.

Likewise, vascular grafts of the present invention may be made with exterior reinforcing in the form of relatively rigid rings, ribs, spirals or other reinforcing structures. Such structures may be made from materials such as non-porous PTFE or FEP. Exterior reinforcement of this type has particular utility in situations where a graft may be vulnerable to external crushing forces or to kinking during bending (such as across a patient's knee).

The void spaces of the graft microstructure may also be loaded with any of a variety of therapeutic substances including anti-thrombotic agents, anti-bacterial agents, gene therapeutic agents, etc., for release into the blood flow or to otherwise improve the properties or performance of the graft. The release rate of these agents may be controlled by various methods known in the art.

The smoothness of the graft luminal surface is measured by profilometry. Measurements are to be taken from representative areas (square areas of 500 microns length on each side) of the smooth luminal surface region of the graft to be considered.

Profilometry measurements are to be performed with a Tencor Profiler Model P-10, measuring samples of square areas of 500 micron length per side. The University of Western Ontario (Room G1), Western Science Centre, London, Ontario, Canada N6A 5B7 has experience making surface measurements with this model profilometer.

Surface data included herein are made using the Tencor Profiler Model P-10 with a MicroHead sr Exchangeable Measurement Head (stylus tip radius of 2.0 microns with an angle of 60°). Menu recipe settings for the profilometer are as follows:

| | |
|---|---|
| Scan length: | 500 microns |
| Scan speed: | 50 microns/second |
| Sampling rate: | 200 Hz |
| No. of traces: | 50 |
| Spacing between traces: | 10 microns |
| No. of points/trace: | 2000 |
| Point interval: | 0.25 microns |
| Stylus force: | 5 mg |

-continued

| Range/resolution: | 65 microns/0.04 Angstroms |
| --- | --- |
| Profile type: | Peaks and valleys |
| Filters: | |
| Waviness filter: | 45 mm/1.8 in. |

Cursors are to be set at each end of the length of each area to be sampled, i.e., at 0 microns and at 500 microns. Scans are performed in the longitudinal direction of tubular samples, i.e., in the direction parallel to the longitudinal axis of the tube. The parameter of concern for surfaces of the present invention is Rq, which is the Root-Mean-Square roughness, defined as the geometric average of the roughness profile from the mean line measured in the sampling length, expressed in units of microns RMS.

The use of an alternative (finer) waviness filter during profilometry allows for materials which include gross surface non-uniformities, such as corrugated surfaces made from microscopically smooth materials.

It is preferred that the grafts of the present invention have luminal surfaces which are smooth in their entirety, i.e., along the entire length of the luminal surface of such a graft. For grafts of relatively uniform surface smoothness along their entire length, surface measurements are preferably made at three points along the length of the luminal surface a graft, specifically at points beginning at one fourth, one half and three fourths of the length of the graft as measured from one end of the graft. For grafts of non-uniform surface character along their entire length, five samples equally spaced along the length should be considered. The measurements from these 3–5 sample areas are then averaged to obtain the surface value for the graft.

For grafts having a densified end, a surface measurement should be made of the luminal surface beginning 0.5 mm from the end edge of the densified end of the graft.

An article entitled "Atomic force microscopy for characterization of the biomaterial interface" describes the use of AFM for consideration of surface smoothness (Siedlecki and Marchant, Biomaterials 19 (1998), pp. 441–454). AFM may be usefully employed for the smoothness evaluation of luminal graft surfaces where the resolution of profilometry is marginally adequate for extremely smooth surfaces. However, for purposes of the present invention, profilometry measurements made using the above-described Tencor profilometer should be adequate for determining the smoothness of graft luminal surfaces.

Mean fibril length (sometimes described as internodal distance or IND) of ePTFE materials having microstructures of nodes interconnected by fibrils is determined as taught by U.S. Pat. No. 5,747,128 to Campbell et al., at col. 6, lines 19–37. Mean fibril length of ePTFE substrate tubes is determined by examination of scanning electron photomicrographs of longitudinal cross sections of the wall of the tube in question.

It is difficult to use the method of the Campbell et al. patent for ePTFE materials which are substantially nodeless (such as ePTFE films described by U.S. Pat. No. 5,476,589 to Bacino). For these types of materials, individual fibril lengths are the lengths of individual fibrils between their points of intersection with other fibrils. Mean fibril lengths of such ePTFE film materials may be effectively estimated by those of ordinary skill by examination of scanning electron photomicrographs of the surfaces of the films.

Matrix tensile strength of ePTFE materials including ePTFE films is measured as taught by U.S. Pat. No. 3,953,566, using an INSTRON tensile testing machine with pneumatic cord and yarn grip jaws, a 25.4 mm wide sample, a 102 mm jaw separation distance and a crosshead speed of 200 mm/minute. The '589 ePTFE films used to construct various examples of the present invention typically have a matrix tensile strength of about 900 MPa when measured in the direction of higher strength.

Bubble point testing is one method of evaluating the porosity of materials. In the bubble point test, liquids with surface free energies less than that of ePTFE can be forced out of the structure with the application of a differential pressure. This clearing of the liquid will occur from the largest passageways first. A passageway is then created through which bulk air flow can take place. The air flow appears as a steady stream of small bubbles through the liquid layer on top of the sample. The pressure at which the first bulk air flow takes place is called the bubble point and is dependent on the surface tension of the test fluid and the size of the largest opening. The bubble point can be used as a relative measure of the structure of a membrane and is often correlated with some other type of performance criteria, such as filtration efficiency or pore size.

The bubble point is measured according to the procedures of ASTM F316–86. Isopropyl alcohol is used as the wetting fluid to fill the pores of the test specimen. The bubble point is the pressure of air required to displace the isopropyl alcohol from the largest pores of the test specimen and create the first continuous stream of bubbles detectable by their rise through a layer of isopropyl alcohol covering the porous media. This measurement provides an estimation of maximum pore size. Typical bubble points for ePTFE materials such as described herein are:

| 1 micron pore size: | 10 psi (0.07 MPa) |
| --- | --- |
| 0.5 micron pore size: | 20 psi (0.14 MPa) |
| 0.1 micron pore size: | 50 psi (0.34 MPa) |
| 0.05 micron pore size: | 200 psi (1.37 MPa) |

For purposes of the present invention, materials which indicate a bubble point value of greater than 50 psi are considered substantially non-porous.

EXAMPLES

Examples of ePTFE tubes of typically 3 mm inside diameter, 0.5 mm wall thickness and various fibril lengths are made for evaluation of surface smoothness and for further luminal surface modification directed to making vascular grafts with smooth PTFE luminal surfaces. These examples are based primarily on ePTFE tubes of 22, 8 and 4 micron mean fibril length, made according to the following descriptions. Some of the resulting ePTFE substrate tubes are provided with luminal surface coverings of ePTFE films, primarily of the '589 type. Some samples are provided with densified ends as described above to allow for implantation without a distal suture line directly exposed to the flow of blood. Various of these grafts are implanted acutely in dogs to ascertain patency and for gross evaluation of the luminal surfaces following retrieval.

While most samples are made using 3 mm inside diameter and 0.5 mm wall thickness, it is apparent that grafts of various diameters and wall thicknesses may be used. In particular, this includes grafts of inside diameters such 0.5 mm, 1.0 mm, 2 mm, 3 mm, 4 mm, 5 mm, 6 mm, 8 mm, 10 mm and larger. Generally, small diameter vascular grafts are considered to be grafts of 6 mm inside diameter or smaller.

The luminal surface smoothness is determined using the above-described Tencor P-10 profilometer and related methodology, for various vascular graft samples including control samples and inventive samples made as described above. These are described in exemplary form as follows:

Example 1

A commercially available GORE-TEX® Vascular Graft (part no. V03030L) is obtained. Surface profilometry indicates a surface value of 3.6489 microns RMS.

Example 2

An inventive graft made from the 22 micron fibril length substrate tube and provided with a luminal layer of ePTFE '589 film is made by the following process.

CD 123 fine powder PTFE resin (obtainable from ICI Americas) is blended with 297 cc of ISOPAR M odorless solvent (Exxon Corp.) per kilogram of PTFE resin, the solvent being intended as an extrusion lubricant. The mixture is compressed into a tubular billet, heated to about 38° C. and extruded into tubes in a ram extruder having a reduction ratio of about 100:1. Lubricant is removed from the extrudate by drying in a first air convection oven set at 260° C. for thirty minutes. The tubes are then expanded by stretching as taught by U.S. Pat. No. 3,953,566. They are stretched 5:1 at a rate of about 400% per second in a second air convection oven set at a temperature of 290° C. Following expansion, the tubes are restrained lengthwise against longitudinal shrinking and then heat treated in a third air convection oven set at 350° C. for a time of about 1.5 minutes. The resulting tubes have mean fibril lengths of about 22 microns. They are used as precursor tubes from which Examples 3–6 are made Example 3

Samples of the 22 micron tube are provided with a luminal surface lining of the '589 ePTFE film as described above. The particular film used is of about 3–5 micron thickness and has a density of about 0.15–0.8, a matrix tensile strength of about 900 MPa and a bubble point of about 25 psi (about 0.17 MPa).

About three wraps of the film are placed onto the surface of a stainless steel mandrel with the direction of higher strength of the film being circumferential to the mandrel surface, after which the 22 micron mean fibril length ePTFE substrate tube of Example 2 is fitted over the wrapped film. An additional, temporary helical wrapping of ePTFE film is provided about the exterior surface of the tube, with the orientation of the higher strength direction of the film again being circumferential with respect to the surface of the mandrel. The purpose of the temporary exterior film wrapping is to radially force the luminal surface of the substrate tube against the luminal film wrapping during the subsequent heating step, during which the assembly is placed into a fourth air convection oven set at about 370° C. for about five minutes. After removal from the oven and being allowed to cool, the temporary film wrapping is removed from the exterior of the graft and the mandrel is removed from the graft lumen.

FIGS. 4A–4C are photomicrographs of this graft wherein FIG. 4A (500x) shows the longitudinal cross section of the wall including the luminal surface and FIGS. 4B and 4C show (500 x and 5000x respectively) the luminal surface. The resulting inventive vascular graft has a surface value of 0.6135 microns RMS as indicated by profilometry. The density of this tube is about 0.7 g/cc.

Example 4

A tube made according to Example 2 is provided with a densified end of about 1.5 cm length made as described preceeding the examples, measured from the point along the wall of the graft where the wall thickness begins to be reduced from a substantially constant value. The resulting tube is then provided with a luminal surface of the '589 ePTFE film in the same manner taught by Example 3.

The exterior surface of the densified end of the graft is provided with a suture ring as shown in FIG. 6 (suture ring 58) by cutting an approximately 1 mm wide section from a length of the graft of Example 2 and slightly stretching the resulting ring diametrically in an amount to allow the ring to be fitted smoothly over a 4 mm diameter mandrel and consequently over the densified graft end. After inserting a 3 mm diameter stainless steel mandrel into the lumen of the full length of the graft for support, a 1 mm wide strip of 0.0005 mm thick FEP film is wrapped circumferentially around the exterior surface of the densified end of the graft at a point beginning about 1.5 cm from the edge of the graft end. The suture ring is then fitted over the wrapping of FEP film, after which the graft and mandrel assembly is placed into a convection air oven set at about 320° C. for a period of about 5 minutes. This period of time is adequate to allow for melting of the FEP in an amount which, following removal of the graft and mandrel assembly from the oven and cooling, results in adhesion of the suture ring to the exterior surface of the densified end of the graft. Following cooling, the graft is cut through transversely about 5 mm from the edge of the suture ring closest to the end. The mandrel is then removed, at which time the transversely cut-off end segment is discarded.

Figure 10:
FIG. 10 is a photomicrograph (5000×) of the smooth luminal surface of the densified end of the graft described in Example 4.

The luminal surface of the densified end is evaluated by profilometry by scanning a 500 micron length sample of that surface beginning 0.5 mm from the end edge of the densified end of the tube and extending toward the center of the length of the tube. This portion of the densified end, when made as described above, is a region of substantially non-porous PTFE which extends inward from the end edge of the tube toward the center of the length of the tube for a distance of 2 to 3 mm. This luminal surface has a surface value of 0.2454 microns RMS. FIG. 10 is a photomicrograph (5000x) of this luminal surface.

Example 5

A similar inventive tube made by the same process as Example 3, using a 22 micron mean fibril length substrate tube according to Example 2 and a slightly different '589 film (having a slightly larger mean fibril length of about 1.6 microns. The resulting graft has a luminal surface value of 1.2400 microns RMS and a density of about 0.7 g/cc.

Example 6

A tube made as described for Example 2 is provided with a densified end of about 1.5 cm length made as described above. The densified end is provided with a suture ring as shown by FIG. 6 (suture ring 58) by the method described for Example 4. Profilometry evaluation is performed by scanning a 500 micron length sample of that surface beginning 0.5 mm from the end edge of the densified end of the tube and extending toward the center of the length of the tube. This portion of the densified end, when made as described above, is a region of substantially non-porous PTFE which extends inward from the end edge of the tube toward the center of the length of the tube for a distance of 2 to 3 mm, and has a surface value of 0.7746 microns RMS.

Example 7

Figure 11:
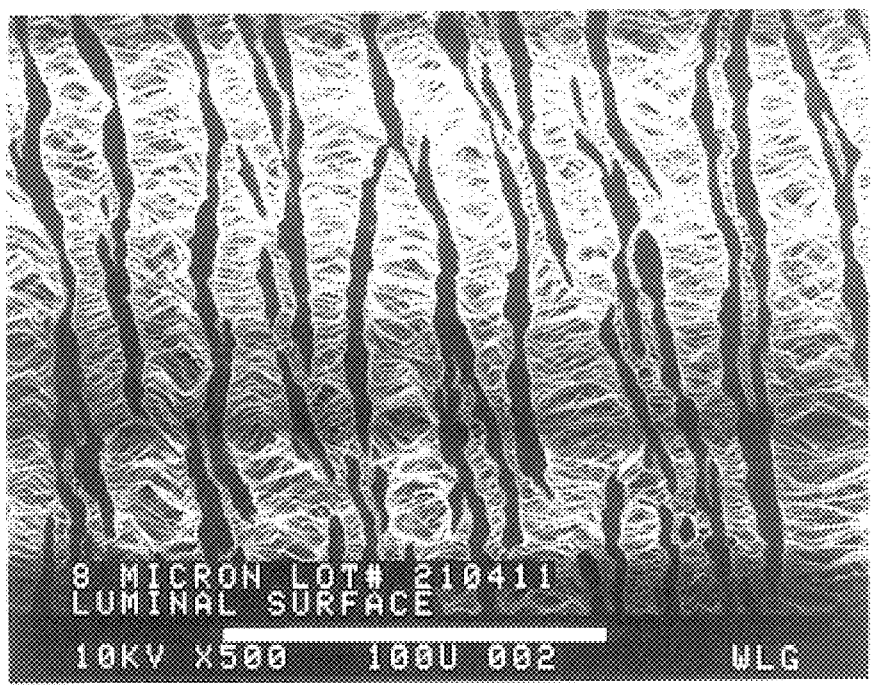
FIG. 11 is a photomicrograph (500×) of the smooth luminal surface of the graft described in Example 7.

Eight micron mean fibril length tubes are manufactured by the same process used for the 22 micron mean fibril length tubes of Example 2, except that the expansion rate is about 125% per second in an amount of 2.2:1. These tubes are not provided with the luminal surface layer of film. An ePTFE tube of about 8 micron mean fibril length, made accordingly, has a surface value of 1.8089 microns RMS and a density of about 0.9 g/cc. FIG. 11 is a photomicrograph (500×) of this luminal surface.

Example 8

A tube made as described for Example 7 is provided with a densified end of about 1.5 cm length made as described above. As with Example 4, the densified end has a region of about 2–3 mm length adjacent the edge of this end which is substantially non-porous PTFE. The luminal surface of the densified end is evaluated by profilometry as described for Example 4. The densified luminal surface has a surface value of 0.7308 microns RMS.

Example 9

Four micron mean fibril length tubes of 4 mm inside diameter are manufactured by the same process used for the 22 micron mean fibril length tubes of Example 2 except for the following differences. The PTFE resin is mixed with about 264 cc of Isopar K odorless solvent (Exxon Corp.) per kilogram of PTFE resin. The compressed tubular billet of blended lubricant and PTFE resin is heated to about 60° C. and extruded into tubes in a ram extruder having a reduction ratio of about 220:1. The resulting tubular extrudate is dried in an air convection oven set at about 130° C. for a time sufficient to remove substantially all of the lubricant. These tubes are expanded 2.2:1 at a rate of about 600% per second in the first forced air convection oven set at a temperature of about 290° C. They are subsequently heat treated in the second convection air oven set at about 370° C. for a time of about 10 minutes.

Figure 12:
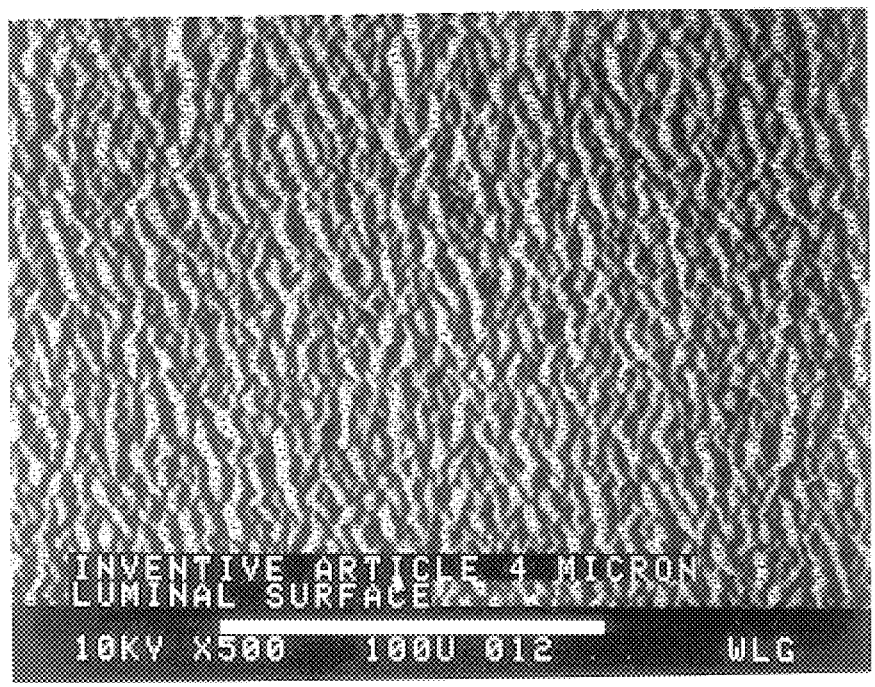
FIG. 12 is a photomicrograph (500×) of the smooth luminal surface of the graft described in Example 9.

The resulting 4 micron mean fibril length ePTFE tube has a surface value of 0.3216 microns RMS and a density of about 1.1 g/cc. FIG. 12 is a photomicrograph (500×) of this luminal surface

Example 10

The luminal surface of a 4 micron mean fibril length tube made as described for Example 9 is further modified by sliding a tight-fitting, polished stainless steel mandrel through the lumen of the graft prior to heat treating on the same mandrel, resulting in burnishing of the surface. During profilometry, the stylus downforce is reduced to 1 mg in order to avoid affecting this thin, burnished surface during the surface value measurement. This burnished luminal surface graft has a surface value of 0.2718 microns RMS.

Example 11

Figure 13:
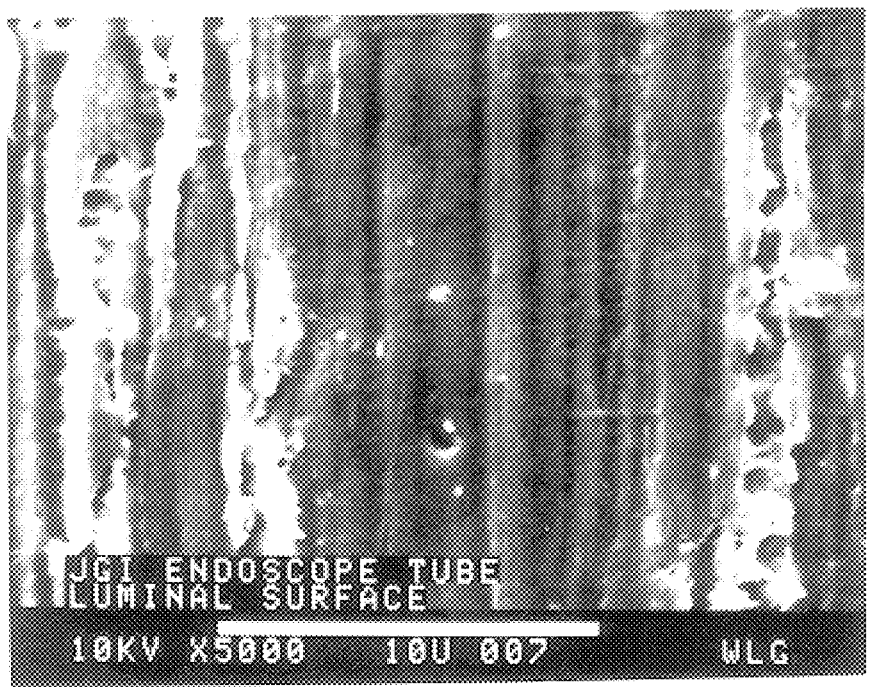
FIG. 13 is a photomicrograph (5000×) of the smooth luminal surface of the tube described in Example 11.

A sample of ePTFE endoscope tubing made as taught by Sasaki et al. in U.S. Pat. No. 5,789,047 has a surface value of 0.5770 microns RMS. However, this tube has a bulk density of 1.55 g/cc, meaning it is of low porosity and correspondingly is relatively inflexible, excessively dense for good handling and too dense to be practically sutured. FIG. 13 is a photomicrograph (5000×) of this luminal surface.

Implant Examples

Various samples of grafts of the present invention are made as described for Examples 1–11 and implanted acutely (for short periods) into canines simultaneously with control grafts. These grafts are implanted interpositionally into the carotid arteries, typically with a control graft on one side and the inventive graft on the contralateral side of the same animal. Ultrasonic flow probes are used to determine blood flow in the grafts and ultimately graft patency, with the flow probes attached distal to the implanted graft. All grafts are tubular, of 3 mm inside diameter and about 0.5 mm wall thickness and about 4 cm length. The control grafts are as described for Example 1, commercially available GORE-TEX® Vascular Grafts (part no. V03030L, W. L. Gore & Associates, Inc., Flagstaff, Ariz.). The inventive grafts of various types are made as described above. Results are presented in Table 1, wherein "+" indicates termination of the study with the majority of the prosthesis still patent.

Generally, it is found that smoother luminal surfaces with densified graft ends resulted in improved graft patency. Additionally, the variation in graft performance also decreases. This reduction in variability is believed to correspond to clot forming on the 8 micron mean fibril length luminal surfaces and subsequently shedding when the clot increases in size to a point where it is released from the luminal surface by blood flow. Alternatively, in the '589 film-lined tube, clot is unable to adhere to the luminal surface in large clumps.

In an additional study, 4 mm inside diameter control and inventive grafts, all without densified ends, are implanted interpositionally in contralateral carotid and femoral arteries of canines for up to 90 days with statistically equivalent patency results (eight grafts of each type in carotids and eight of each type in femorals, see Table 2). Control grafts were as per Example 1 except that they were of 4 mm inside diameter. The inventive grafts are according to Example 3, i.e., 22 micron mean fibril length ePTFE tubes provided with a luminal surface lining of the above-described '589 ePTFE film. Light microscopic examination of the explanted prostheses shows a thin monolayer of endothelial cells covering most of the luminal surface areas of the inventive grafts (7 of a total of 10 examined grafts). Areas which are rougher textured, caused by rougher regions of the underlying 22 micron substrate tube, correspond to areas of thrombus and leukocyte deposition. The luminal surfaces of the Example 1 control grafts are entirely covered with fibrin and are not endothelialized. At 90 days the gross appearance of the inventive grafts was better than the gross appearance of the control grafts in 9 of 11 patent pairs, and was equivalent in 2 of 11 patent pairs. In no case was the gross appearance of the control grafts better than the gross appearance of the inventive grafts (see Table 2).

TABLE 1

| | Acute results | |
|---|---|---|
| Graft type | # Patent at Retrieval/ # Implanted | Average Time to Failure (min) |
| Example 1 (control) | 2/19 | 50 |
| Example 3 | 1/4 | 60 |
| Example 4 | 3/4 | 218+ |
| Example 6 | 0/8 | 40 |
| Example 7 | 0/1 | 40 |
| Example 8 | 8/9 | 128+ |

TABLE 2

| | Chronic results | |
|---|---|---|
| Observation | Control Grafts | Inventive Grafts |
| No. of grafts with better gross appearance (patent pairs only) | 0/11 | 9/11 |
| Patent at 90 days | 15/16 | 12/16 |
| No. endothelized (10 patent pairs examined) | 0/10 | 7/10 |

We claim:

1. A vascular graft comprising: a substrate; and a luminal surface comprising polytetrafluoroethylene provided to the substrate, the luminal surface having a surface value of about 1.7 microns RMS, or less; and the luminal surface being oriented as a blood contact surface for the vascular graft.

2. A vascular graft according to claim 1 having a luminal surface with a surface value of about 1.6 microns RMS or less.

3. A vascular graft according to claim 1 having a luminal surface with a surface value of about 1.4 microns RMS or less.

4. A vascular graft according to claim 1 having a luminal surface with a surface value of about 1.2 microns RMS or less.

5. A vascular graft according to claim 4 wherein the luminal surface comprises a film of porous expanded polytetrafluoroethylene having a microstructure of interconnected fibrils.

6. A vascular graft according to claim 4 wherein the luminal surface has a substrate comprising a porous expanded polytetrafluoroethylene tube having a mean fibril length between about 5 and 90 microns.

7. A vascular graft according to claim 4 wherein the vascular graft comprises a cardiovascular patch.

8. A vascular graft according to claim 4 wherein the vascular graft comprises an intraluminal graft.

9. A vascular graft according to claim 4 wherein the vascular graft comprises a covering over at least a portion of a stent's exterior surface.

10. A vascular graft according to claim 4 wherein the vascular graft comprises a covering over at least a portion of a stent's luminal surface.

11. A vascular graft according to claim 1 having a luminal surface with a surface value of about 1.0 microns RMS or less.

12. A vascular graft according to claim 11 wherein the luminal surface comprises a film of porous expanded polytetrafluoroethylene having a microstructure of interconnected fibrils.

13. A vascular graft according to claim 11 wherein the luminal surface has a substrate comprising a porous expanded polytetrafluoroethylene tube having a mean fibril length between about 5 and 60 microns.

14. A vascular graft according to claim 11 wherein the vascular graft comprises a cardiovascular patch.

15. A vascular graft according to claim 11 wherein the vascular graft comprises an intraluminal graft.

16. A vascular graft according to claim 11 wherein the vascular graft comprises a covering over at least a portion of a stent's exterior surface.

17. A vascular graft according to claim 11 wherein the vascular graft comprises a covering over at least a portion of a stent's luminal surface.

18. A vascular graft according to claim 1 having a luminal surface with a surface value of about 0.8 microns RMS or less.

19. A vascular graft according to claim 1 having a luminal surface with a surface value of about 0.6 microns RMS or less.

20. A vascular graft according to claim 1 having a luminal surface with a surface value of about 0.4 microns RMS or less.

21. A vascular graft according to claim 1 wherein said vascular graft is microporous having void spaces which contain a therapeutic agent.

22. A vascular graft according to claim 1 wherein said vascular graft is capable of being stretched and then rapidly recovering more than about 6% of its stretched length.

23. A vascular graft according to claim 1 having a density of less than about 1.2 g/cc.

24. A vascular graft according to claim 23 wherein said luminal surface has a surface value of about 1.2 microns RMS or less.

25. A vascular graft according to claim 23 wherein said luminal surface has a surface value of about 1.0 microns RMS or less.

26. A vascular graft according to claim 23 wherein said luminal surface has a surface value of about 0.6 microns RMS or less.

27. A vascular graft according to claim 23 wherein said vascular graft has a density of less than about 1.0 g/cc.

28. A vascular graft according to claim 27 wherein said luminal surface has a surface value of about 1.2 microns RMS or less.

29. A vascular graft according to claim 27 wherein said luminal surface has a surface value of about 1.0 microns RMS or less.

30. A vascular graft according to claim 27 wherein said luminal surface has a surface value of about 0.6 microns RMS or less.

31. A vascular graft according to claim 23 wherein said vascular graft has a density of less than about 0.8 g/cc.

32. A vascular graft according to claim 31 wherein said luminal surface has a surface value of about 1.2 microns RMS or less.

33. A vascular graft according to claim 31 wherein said luminal surface has a surface value of about 1.0 microns RMS or less.

34. A vascular graft according to claim 31 wherein said luminal surface has a surface value of about 0.6 microns RMS or less.

35. A vascular graft according to claim 1 wherein said luminal surface comprises a layer of porous expanded polytetrafluoroethylene film.

36. A vascular graft according to claim 35 wherein said porous expanded polytetrafluoroethylene film comprises a network of interconnected fibrils wherein said film has a direction of higher strength which is substantially perpendicular to a longitudinal axis of the tube.

37. A vascular graft according to claim 35 wherein said porous expanded polytetrafluoroethylene film provides a luminal surface having a surface value of less than about 1.2 microns RMS.

38. A vascular graft according to claim 35 wherein said porous expanded polytetrafluoroethylene film comprises a network of interconnected fibrils wherein said film has a direction of higher strength oriented substantially parallel to the longitudinal axis of the tube.

39. A vascular graft according to claim 35 wherein said substrate tube comprises porous expanded polytetrafluoroethylene.

40. A vascular graft according to claim 39 wherein said film has a mean fibril length substantially less than a. mean fibril length of the porous expanded polytetrafluoroethylene tube.

41. A vascular graft according to claim 35 wherein the film layer has a seam extending between ends of the substrate.

42. A vascular graft according to claim 35 wherein said luminal surface has a surface value of about 1.2 microns RMS or less.

43. A vascular graft according to claim 35 wherein said luminal surface has a surface value of about 0.6 microns RMS or less.

44. A method of using a vascular graft wherein said vascular graft comprises a substrate having a luminal surface of polytetrafluoroethylene provided to the substrate and wherein the luminal surface has a surface value of about 1.7 microns RMS or less, said method comprising implanting said vascular graft in a living body with the luminal surface in contact with blood.

45. A method of using a vascular graft according to claim 44 wherein the luminal surface has a surface value of about 1.6 microns RMS or less.

46. A method of using a vascular graft according to claim 44 wherein the luminat surface has a surface value of about 1.4 microns RMS or less.

47. A method of using a vascular graft according to claim 44 wherein the luminal surface has a surface value of about 1.2 microns RMS or less.

48. A method of using a vascular graft according to claim 47 wherein the luminal surface comprises a film of porous expanded polytetrafluoroethylene having a microstructure of interconnected fibrils.

49. A method of using a vascular graft according to claim 47 wherein the luminal surface has a substrate comprising a porous expanded polytetrafluoroethylene tube having a mean fibril length between about 5 and 90 microns.

50. A method of using a vascular graft according to claim 47 wherein the vascular graft comprises a cardiovascular patch.

51. A method of using a vascular graft according to claim 47 wherein the vascular graft comprises an intraluminal graft.

52. A method of using a vascular graft according to claim 47 wherein the vascular graft comprises a covering over at least a portion of a stent's exterior surface.

53. A method of using a vascular graft according to claim 47 wherein the vascular graft comprises a covering over at least a portion of a stent's luminal surface.

54. A method of using a vascular graft according to claim 47 wherein the luminal surface has a surface value of about 1.0 microns RMS or less.

55. A method of using a vascular graft according to claim 54 wherein the luminal surface comprises a film of porous expanded polytetrafluoroethylene having a microstructure of interconnected fibrils.

56. A method of using a vascular graft according to claim 54 wherein the luminal surface has a substrate comprising a porous expanded polytetrafluoroethylene tube having a mean fibril length between about 5 and 60 microns.

57. A method of using a vascular graft according to claim 54 wherein the vascular graft comprises a cardiovascular patch.

58. A method of using a vascular graft according to claim 54 wherein the vascular graft comprises an intraluminal graft.

59. A method of using a vascular graft according to claim 54 wherein the vascular graft comprises a covering over at least a portion of a stent's exterior surface.

60. A method of using a vascular graft according to claim 54 wherein the vascular graft comprises a covering over at least a portion of a stent's luminal surface.

61. A method of using a vascular graft according to claim 44 wherein the luminal surface has a surface value of about 0.8 microns RMS or less.

62. A method of using a vascular graft according to claim 44 wherein the luminal surface has a surface value of about 0.6 microns RMS or less.

63. A method of using a vascular graft according to claim 44 wherein the luminal surface has a surface value of about 0.4 microns RMS or less.

64. A method of using a vascular graft according to claim 44 wherein said vascular graft is microporous having void spaces which contain a therapeutic agent.

65. A method of using a vascular graft according to claim 44 wherein said vascular graft is capable of being stretched and then rapidly recovering more than about 6% of its stretched length.

66. A method of using a vascular graft according to claim 44 wherein said vascular graft has a density of less than about 1.2 g/cc.

67. A method of using a vascular graft according to claim 66 wherein said luminal surface has a surface value of about 1.2 microns RMS or less.

68. A method of using a vascular graft according to claim 66 wherein said luminal surface has a surface value of about 1.0 microns RMS or less.

69. A method of using a vascular graft according to claim 66 wherein said luminal surface has a surface value of about 0.6 microns RMS or less.

70. A method of using a vascular graft according to claim 66 wherein said vascular graft has a density of less than about 1.0 g/cc.

71. A method of using a vascular graft according to claim 70 wherein said luminal surface has a surface value of about 1.2 microns RMS or less.

72. A method of using a vascular graft according to claim 70 wherein said luminal surface has a surface value of about 1.0 microns RMS or less.

73. A method of using a vascular graft according to claim 70 wherein said luminal surface has a surface value of about 0.6 microns RMS or less.

74. A method of usirg a vascular graft according to claim 66 wherein said vascular graft has a density of less than about 0.8 g/cc.

75. A method of using a vascular graft according to claim 74 wherein said luminal surface has a surface value of about 1.2 microns RMS or less.

76. A method of using a vascular graft according to claim 74 wherein said luminal surface has a surface value of about 1.0 microns RMS or less.

77. A method of using a vascular graft according to claim 74 wherein said luminal surface has a surface value of about 0.6 microns RMS or less.

78. A method of using a vascular graft according to claim 44 wherein said luminal surface comprises a layer of porous expanded polytetrafluoroethylene film.

79. A method of using a vascular graft according to claim 78 wherein said porous expanded polytetrafluoroethylene film comprises a network of interconnected fibrils wherein said film has a direction of higher strength which is substantially perpendicular to a longitudinal axis of the tube.

80. A method of using a vascular graft according to claim 78 wherein said porous expanded polytetrafluoroethylene film provides a luminal surface having a surface value of less than about 1.2 microns RMS.

81. A method of using a vascular graft according to claim 78 wherein said porous expanded polytetrafluoroethylene film comprises a network of interconnected fibrils wherein said film has a direction of higher strength oriented substantially parallel to the longitudinal axis of the tube.

82. A method of using a vascular graft according to claim 78 wherein said substrate tube comprises porous expanded polytetrafluoroethylene.

83. A method of using a vascular graft according to claim 82 wherein said film has a mean fibri length substantially less than a mean fibril length of the porous expanded polytetrafluoroethylene tube.

84. A method of using a vascular graft according to claim 78 wherein the film layer has a seam extending between ends of the substrate.

85. A method of using a vascular graft according to claim 78 wherein said luminal surface has a surface value of about 1.0 microns RMS or less.

86. A method of using a vascular graft according to claim 78 wherein said luminal surface has a surface value of about 0.6 microns RMS or less.

* * * * *